(12) United States Patent
Niizeki et al.

(10) Patent No.: US 6,398,741 B2
(45) Date of Patent: *Jun. 4, 2002

(54) TISSUE EXCISION AND CUTTING APPARATUS AND ITS FORCEPS

(75) Inventors: Ryuichiro Niizeki; Masaya Tatsumi, both of Kyoto (JP)

(73) Assignee: J. Morita Manufacturing Corporation, Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/439,760

(22) Filed: Nov. 15, 1999

(30) Foreign Application Priority Data

Nov. 20, 1998 (JP) .............................. 10-331358
Mar. 23, 1999 (JP) .............................. 11-078436

(51) Int. Cl.⁷ .............................................. A61B 17/32
(52) U.S. Cl. ...................... 600/566; 606/207; 606/184; 606/180; 600/567
(58) Field of Search ................................. 606/184, 170, 606/205, 207; 600/566, 567

(56) References Cited

U.S. PATENT DOCUMENTS

| | | | | |
|---|---|---|---|---|
| 1,659,112 A | * | 2/1928 | Littlejohn | 606/205 |
| 4,289,133 A | * | 9/1981 | Rothfuss | 606/184 |
| 4,641,651 A | * | 2/1987 | Card | 606/184 |
| 5,171,250 A | * | 12/1992 | Yoon | 606/170 |
| 5,281,230 A | * | 1/1994 | Heidmueller | 606/207 |
| 5,439,474 A | * | 8/1995 | Li | 606/184 |
| 5,520,634 A | * | 5/1996 | Fox et al. | 606/170 |
| 5,665,100 A | * | 9/1997 | Yoon | 606/170 |
| 5,800,449 A | * | 9/1998 | Wales | 606/205 |
| 5,827,316 A | * | 10/1998 | Young et al. | 606/184 |
| 5,931,810 A | * | 8/1999 | Grabek | 606/205 |
| 6,022,324 A | * | 2/2000 | Skinner | 600/566 |
| 6,039,748 A | * | 3/2000 | Savage et al. | 606/184 |
| 6,099,550 A | * | 8/2000 | Yoon | 606/207 |

* cited by examiner

Primary Examiner—Michael H. Thaler
(74) Attorney, Agent, or Firm—Koda & Androlia

(57) ABSTRACT

A tissue excision and cutting apparatus used by being inserted into a trocar for cutting off a part of tissue as a sample piece for such a diagnosis in a laparoscopic surgery or the like. The apparatus comprises a resection blade having an inner hollow cylinder with a cutting blade at its tip end, and a forceps having at its tip end a clamp having a movable jaw capable of opening and closing which is joined to a fixed jaw with a chopping block piece, open-close mechanism having an operation part for opening and closing the movable jaw, and a longitudinal penetrating passage into which the resection blade is inserted and moves back and forth therein.

11 Claims, 21 Drawing Sheets

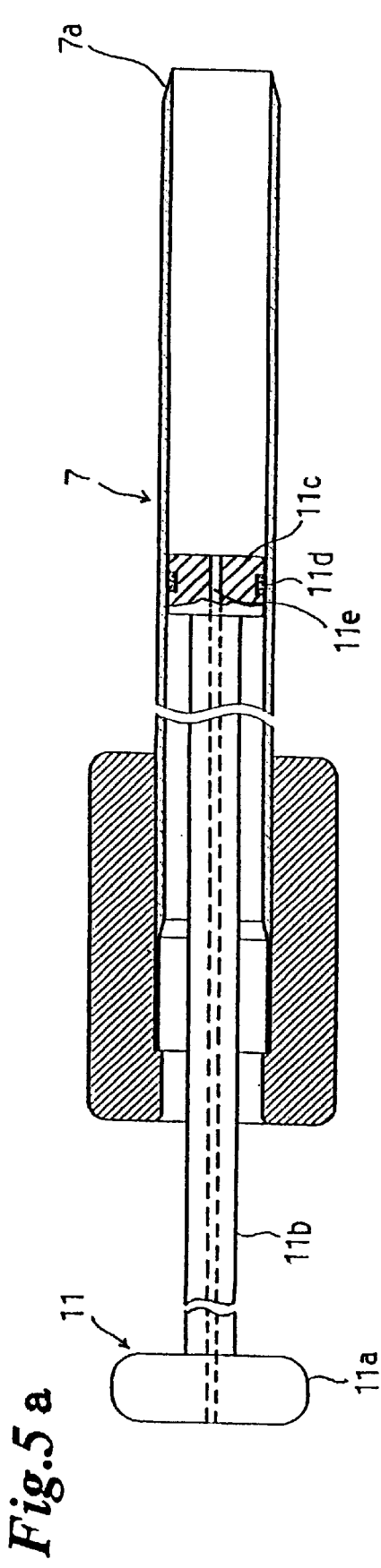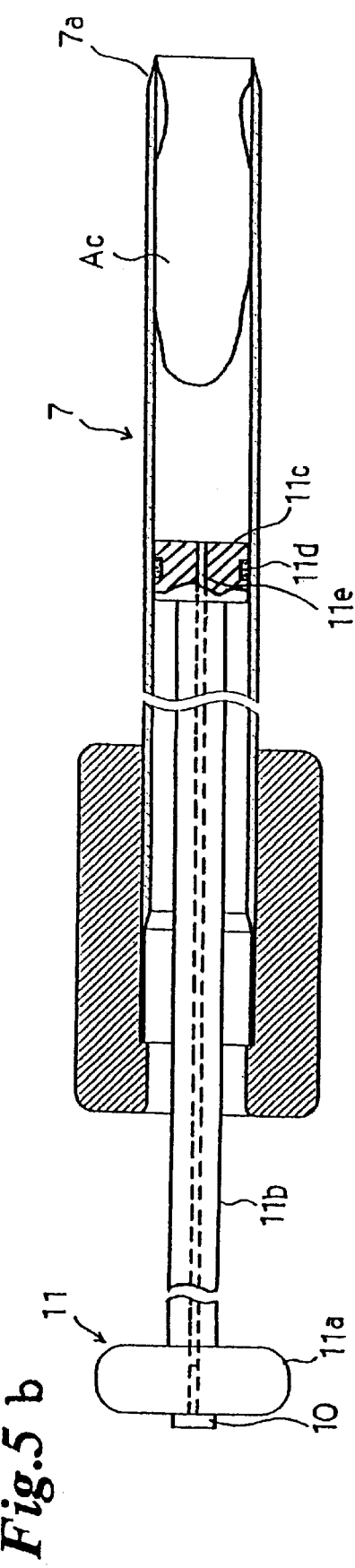
Fig.5 a
Fig.5 b

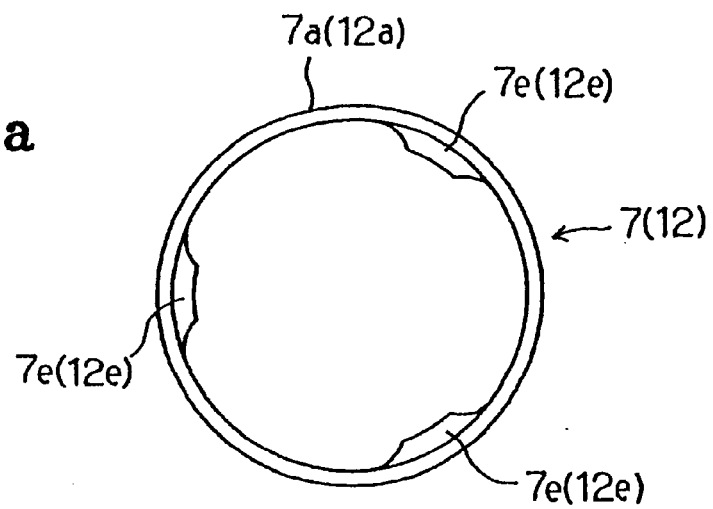
*Fig.14* a
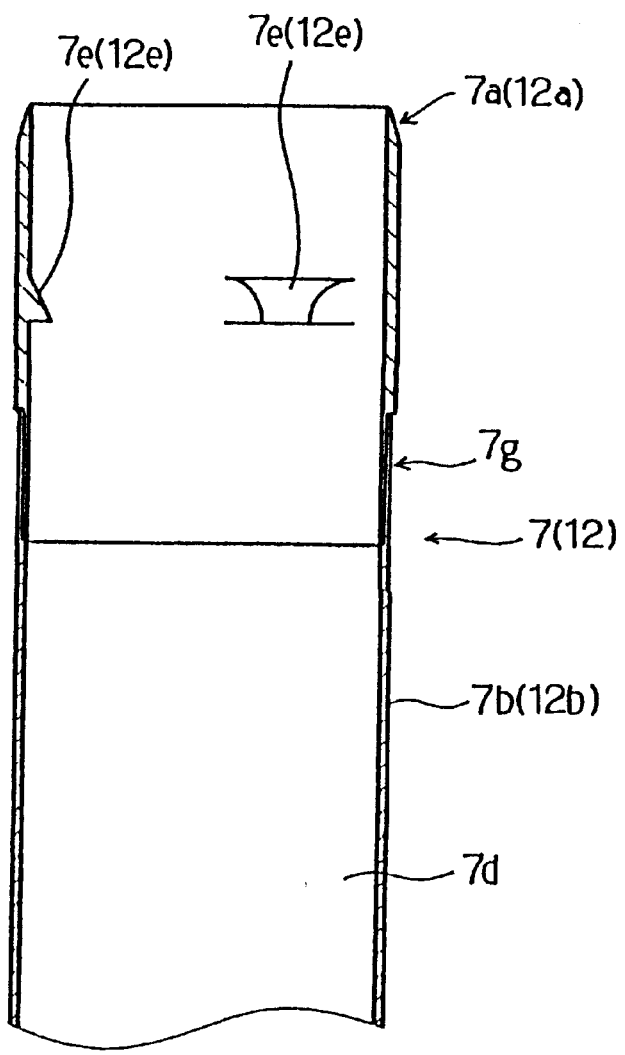
*Fig.14* b

*Fig.16* a
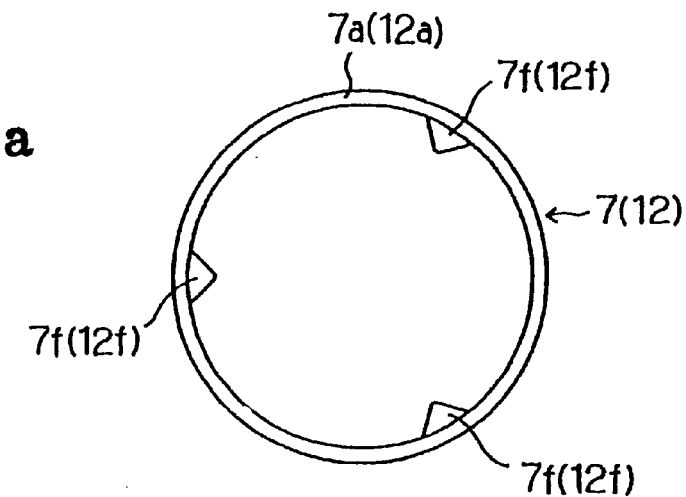
*Fig.16* b
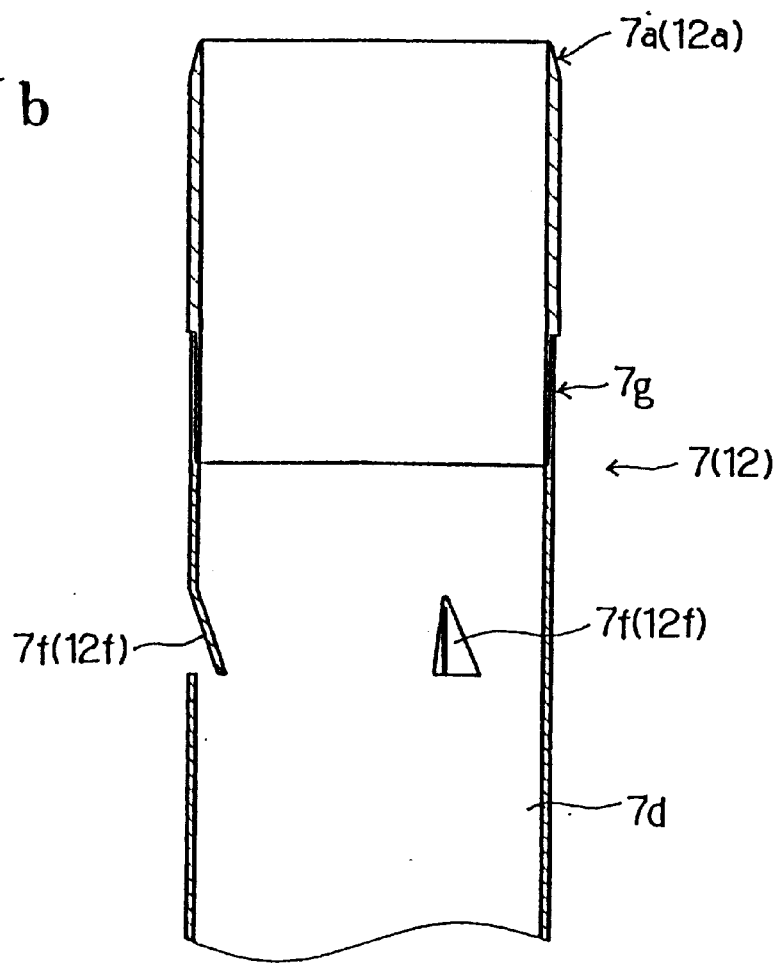

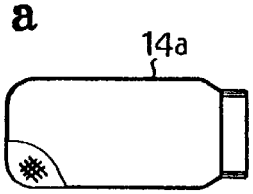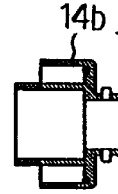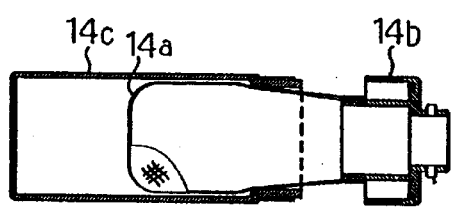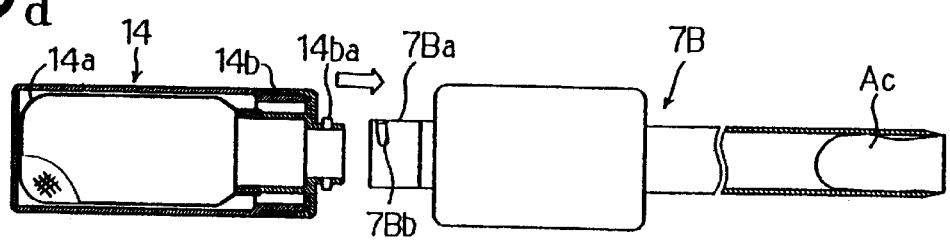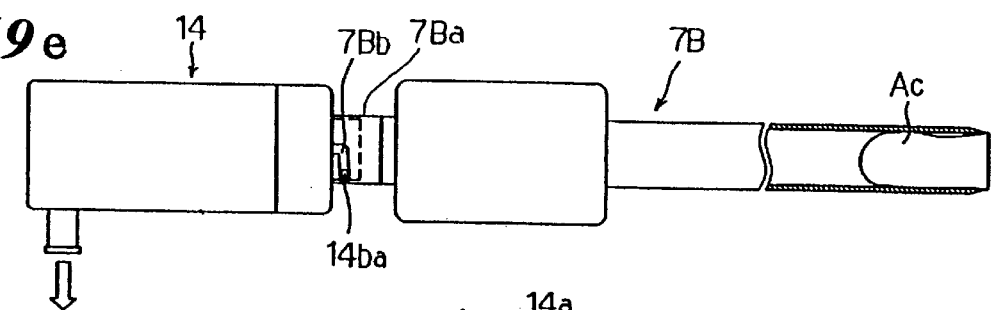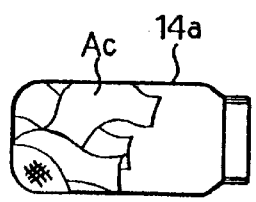

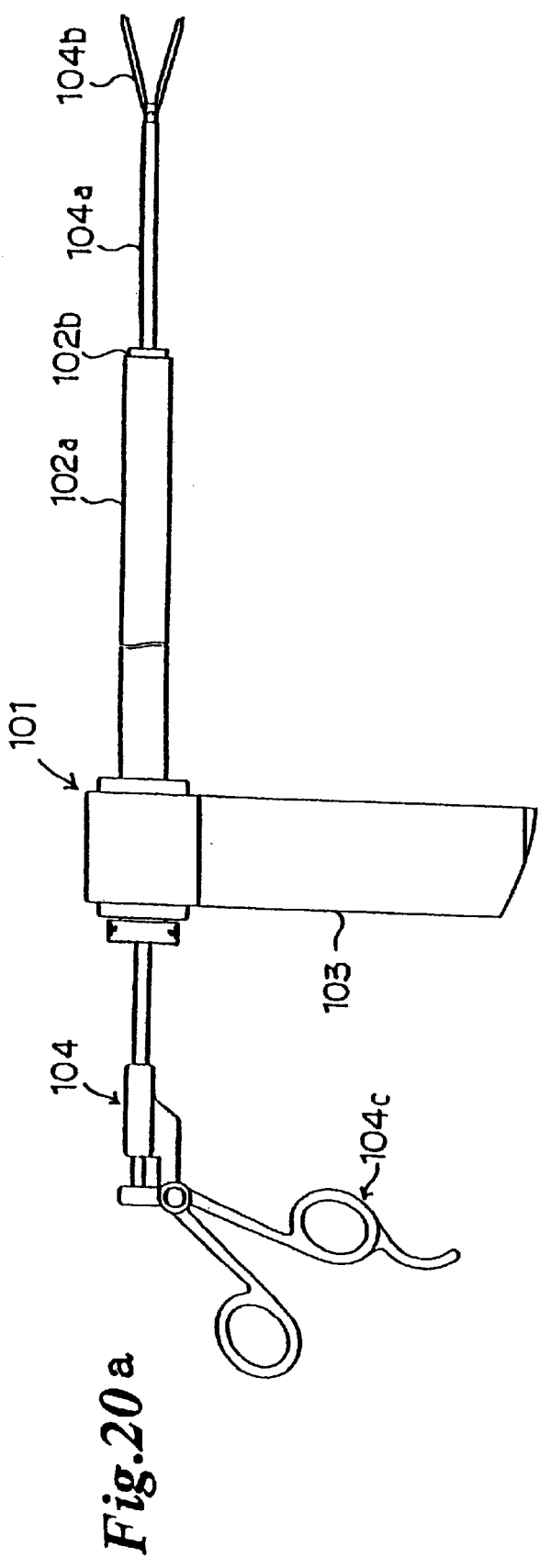
*Fig.20* a
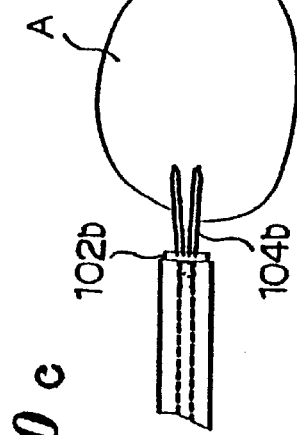
*Fig.20* c
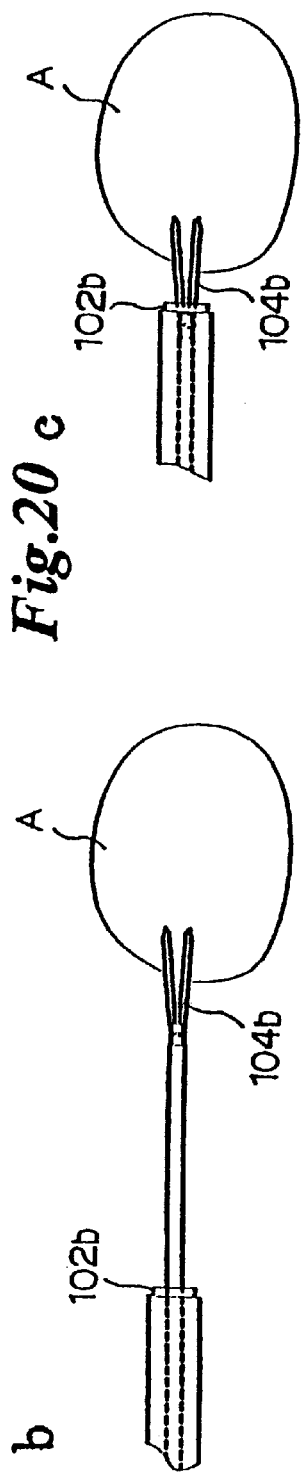
*Fig.20* b

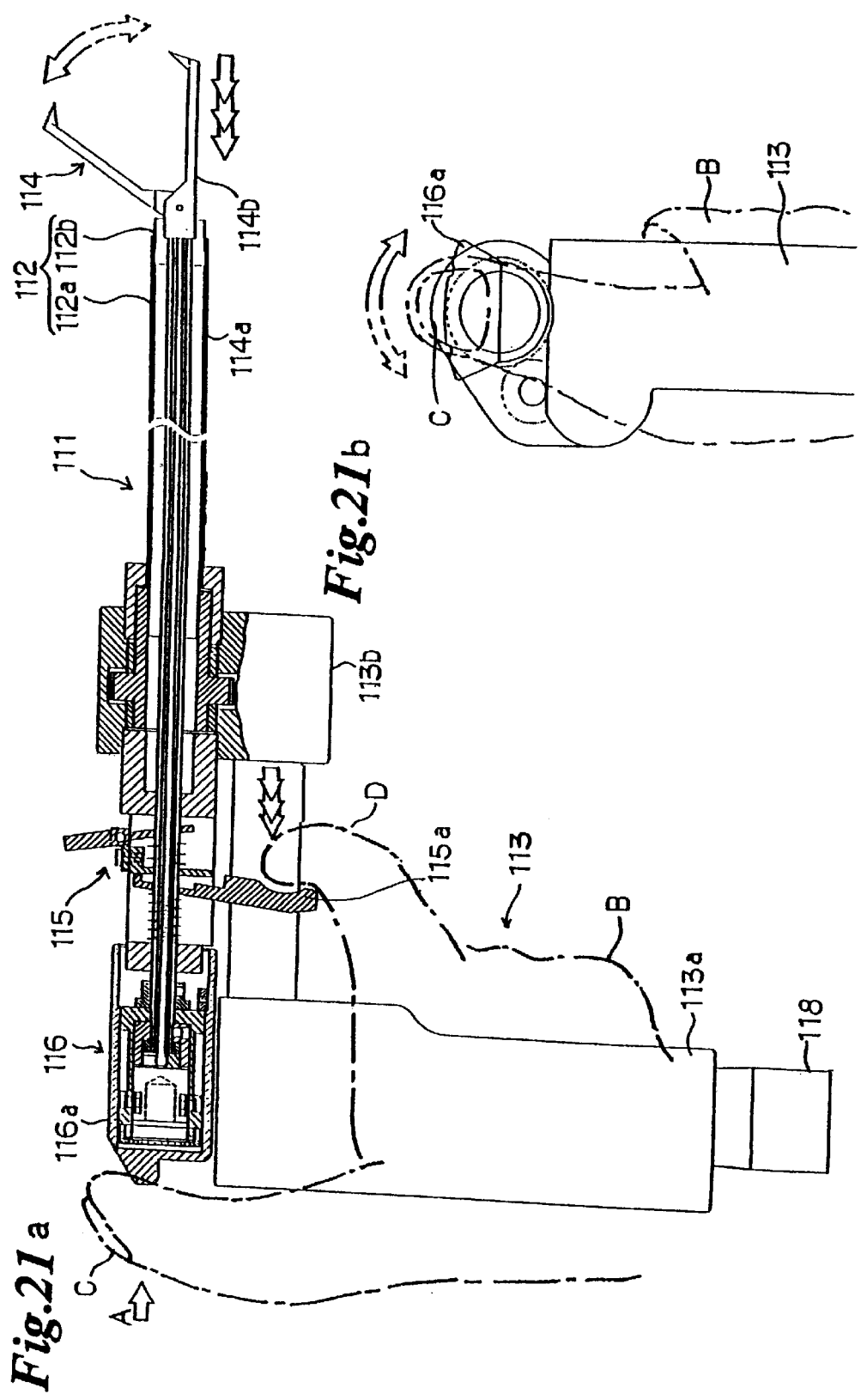

TISSUE EXCISION AND CUTTING APPARATUS AND ITS FORCEPS

FIELD OF THE INVENTION

The present invention relates to a newly developed tissue excision and cutting apparatus and resection forceps for cutting off a part of human tissue as a sample piece for such a diagnosis in laparoscopic surgery or the like.

PRIOR ART

A tissue excision and cutting apparatus for surgical operation has been used together with a forceps and a laparoscope and various kinds of such related apparatuses have been proposed till up now.

One example has a cylindrical resection blade rotated by a motor in a guide cylinder to be inserted into a trocar, and forceps for grasping an objective tissue inserted into the resection blade.

FIGS. 20a to 20c show how to use the tissue excision and cutting apparatus of prior art and the forceps to be combined therewith.

A tissue excision and cutting apparatus 101, as shown in FIG. 20a, comprises a main body 103 with grip portion, a guide cylinder 102a to be inserted into a trocar (not shown), and a resection blade 102b with a blade at its tip end which is driven to be rotated in the guide cylinder 102a by a motor (not shown).

On the other hand, a forceps 104 to be combined with the tissue excision and cutting apparatus 101 in such a manner as shown in FIG. 20(a) has a main axis 104a with at its tip end a clamp 104b which can be opened and closed by manual operation of one hand.

According to such a tissue excision and cutting apparatus 101, while observing around the tip end of the tissue excision and cutting apparatus 101 inserted into the trocar by a laparoscope (not shown), a tissue A may be grasped by the clamp 104b of the forceps 104 by approaching the forceps to the tissue A, after then the forceps 104 is withdrawn into the guide cylinder 102a in the state of grasping tissue A to bring it into contact with the blade of rotating resection blade 102b, by which a part of tissue A can be cut off as a sample piece (See FIGS. 20a to 20c).

FIG. 21 shows a tissue excision and cutting apparatus according to the prior art in which a forceps and a resection blade are integrated wherein FIG. 21a illustrates a front view of its partial vertical section and FIG. 21b its rear view.

A tissue excision and cutting apparatus 111, as shown in these figures, comprises a tissue cutting resection blade 112 composed of a cylindrical blade 112b and a guide cylinder 112a, a main body 113 with a grip 113a and holing portion 113b for the forceps 114, a forceps 114 itself, a forceps withdrawing mechanism 115 with a trigger 115a for finger operation, a forceps open-close mechanism 116 with a finger operation part 116a, and a motor 118 for rotating the blade 112b.

In this figure, turning operational direction of the open-close finger operation part 116a is shown as an arrow corresponding to open and close operations of the clamp 114b wherein opening direction is shown as an actual line and closing direction is shown as a dotted line, whereas sequential pulling operation of the trigger 115a is also shown by an arrow corresponding to withdrawing operation of the forceps.

According to such a tissue excision and cutting apparatus 111, operating a laparoscope (not shown) by a left hand while observing objective tissue with the apparatus 111 held by a right hand, and advancing the forceps 114 to the objective tissue, where the open-close operation part 116a is turned in a closing direction by a thumb C of the right B hand as shown in a dotted line in FIG. 21(b), thus enabling to grasp the objective tissue by the clamp 114b of the forceps 114.

After grasping the tissue A, the motor 118 is driven to rotate resection blade 112b and the trigger 115a is repeatedly operated by a forefinger D of the right hand B, thereby cutting off tissue A by the resection blade 112b in cylindrical shape. And the apparatus is so constructed that tissue thus grasped is prevented from dropping out even if the thumb C is departed from the open-close operation part 116a.

According to the tissue excision and cutting apparatus 111 described above, comparing to the one shown in FIG. 20, the forceps can be operated by a thumb C and retraction can be executed by a forefinger D, with its main body held only by one hand, thus enabling another hand to operate a laparoscope or the like.

In any of above-mentioned tissue excision and cutting apparatus of the prior art, tissue is drawn into a guide cylinder and cut off therein while rotating a resection blade. Therefore, in such a method, tissue would not be sharply or finely cut off.

In other words, in such a method tissue is apt to be torn off and partly broken when tissue is drawn into the guide cylinder to be cut off so that it makes difficult to surely and sharply cut off the tissue, or the part of tissue could not be cut off well.

In addition, in such a prior tissue excision and cutting apparatus, the resection blade is exposed from a guide cylinder when tissue is cut off. Therefore, there would be a fear that organ not to be cut off or an end-bag (explained hereinafter referring to FIG. 6 to FIG. 9) used for laparoscopic surgery happens to be damaged.

SUMMARY OF THE INVENTION

The present invention has proposed to solve the above-mentioned problems.

Accordingly, it is the primary object of the invention to provide a tissue excision and cutting apparatus which can finely and sharply cut off an objective tissue and a resection forceps to be used for the apparatus.

It is another object to provide a tissue excision and cutting apparatus which doesn't have such a fear and a forceps used for the apparatus.

In the present invention, a tissue excision and cutting apparatus used by inserted into a trocar for cutting off a part of tissue for sampling in laparoscopic surgery or the like comprises a resection blade with an inner hollow cylinder body having a cutting blade at its tip end, and a forceps for cutting off a part of tissue to be cut off as a sample piece.

The forceps has at its tip end a clamp for grasping a part of tissue which has a movable jaw capable of opening and closing and is joined to a fixed jaw vertically provided with a chopping block piece, an open-close mechanism with a hand operation part for opening and closing by manual operation, and a longitudinal penetrating passage into which the resection blade is inserted and moves back and forth therein.

The tissue excision and cutting apparatus is constructed such that resection blade and the forceps are combined with when using it.

The apparatus is characterized in that the penetrating passage of the forceps is constructed such that the resection blade is inserted into and moves back and forth therein and one of the clamp of the forceps is a fixed jaw provided at its chip end with a chopping block piece servicing as a stopper plate for the blade of resection blade. The chopping block piece functions as the so called chopping block for the blade of the resection blade, thereby enabling to cut off an objective tissue by pressing it in such manner as not in the prior pull-in-type tissue excision and cutting apparatus, thus any of tissues can be finely and surely cut off.

In addition, in the apparatus, other organ or an endo-bag isn't damaged because the resection blade is contained and hidden in the clamp of the forceps, thereby achieving safety.

If the shape of a part where the resection blade is contacted is contrived, tissue can be cut off not only by pressing on the resection blade a chopping block piece but also by shearing the resection blade and the chopping block piece. For example, when the chopping block piece is normally formed as such cylindrical shape that it has an inner diameter in which the outer diameter of cylindrical blade of the resection blade is just engaged, tissue can be sheared to be cut off by cylindrical shape, or the chopping block piece and the resection blade.

In other embodiment of the present invention, a tissue excision and cutting apparatus used by inserted into a trocar for cutting off a part of tissue for sampling in laparoscopic surgery or the like comprises a resection blade with an inner hollow cylinder body having a cutting blade at its tip end, and a forceps for cutting off a part of tissue as a sample piece wherein the resection blade is capable of rotating by driving a rotary driving mechanism and the forceps has at its tip end a clamp for grasping a part of tissue to be cut off which has a movable jaw capable of opening and closing and is joined to a fixed jaw vertically provided with a chopping block piece, an open-close mechanism with a hand operation part for opening and closing by manual operation, and a longitudinal penetrating passage into which the resection blade is inserted and moves back and forth therein.

According to such a tissue excision and cutting apparatus, the resection blade is capable of rotating by a rotary driving mechanism comprised of a motor by operating a switching means such a foot pedal or the like. Therefore, tissue can be cut off and sampled more smoothly.

Further in another tissue excision and cutting apparatus of the present invention, the hand operation part of the forceps is constructed such that it can be held by one hand and the movable jaw can be operated by the one hand. Therefore, the apparatus is very convenient for handling because forceps can be held and manually operated by one hand while the resection blade can be operated by another hand.

Further in other embodiment of the present invention, a chopping block piece of the resection blade is formed with a blade receiving surface on which the whole circumference of the blade contacts.

According to such construction, cut end of tissue by the resection blade can be done sharply and finely by pressing the blade of the resection blade onto the surface.

In still another embodiment of the invention, a sealing mechanism for airtightly sealing the penetrating passage is further provided for isolating ventilation of the open air even when the forceps is inserted into the passage or is pulled out from the passage.

According to such construction, outer air is prevented from entering in abdominal cavity or the endo-bag through the penetrating passage or especially pneumoperitoneum gas is prevented from leaking out when being filled in the endo-bag.

In other embodiment of the invention, the sealing valve mechanism is detachable and exchangeable for the penetrating passage.

Therefore, used it is very useful for preventing contamination or contagion since it can be easily exchanged every time the forceps is used.

In still other embodiment of the invention, the resection blade further comprises a sealing rod for airtightly sealing the inner of the hollow cylinder body and a push shaft for outward extruding a part of tissue cut off and held in the hollow cylinder body as a sample piece which is airtightly inserted into the cylinder body from a push hole provided at the rear end of the sealing rod.

According to such tissue excision and cutting apparatus, the inner of the hollow cylinder body of the resection blade can be kept airtight by the sealing rod and the push rod so that the tissue cut off as a sample piece is prevented from dropping out from the hollow cylinder body even when the tip of the resection blade is directed downward for extracting the resection blade from the forceps. And the cut off tissue held in the hollow cylinder body can be easily extruded by releasing the sealing and pushing the push shaft into the inner of the hollow cylinder after when the resection blade is moved to a predetermined place.

In other embodiment of the invention, the resection blade further comprises a sealing push rod airtightly inserted into the hollow cylinder body from an insertion opening provided at the rear end of the cylinder body, and a simple suction means which is connected to the sealing push rod for keeping the inner portion of the hollow cylinder body airtight to hold a part of tissue cut off by the resection blade.

According to such tissue excision and cutting apparatus, the cut off tissue as a sample piece held in the hollow cylinder body can be surely prevented from dropping out by effecting sucking force by means of the simple suction means. Further, the cut off tissue held in the hollow cylinder body can be easily extruded outward by releasing the sucking force and pushing a sealing push rod into the hollow cylinder body after moving to a predetermined place.

In still further other embodiment of the tissue excision and cutting apparatus, the resection blade further comprises a sealing suction rod into which a sealing suction mechanism is incorporated and a push rod for outward extruding the tissue cut off and held in the hollow cylinder body as a sample piece wherein the sealing suction rod airtightly seals the inner portion of the hollow cylinder and holds the tissue by keeping airtight, and the push rod is airtightly inserted in the hollow cylinder body from a push hole provided at the rear end of the sealing suction rod.

According to such tissue excision and cutting apparatus, the cut off tissue as a sample piece held in the hollow cylinder body can be surely prevented from dropping out by effecting sucking force by means of the simple suction means. Further, the cut off tissue held in the hollow cylinder body can be easily extruded outward by releasing the sucking force and pushing a sealing push rod into the hollow cylinder body after moving to a predetermined place. In addition, it is more convenient to handle it because sealing suction rod and a sealing suction mechanism are incorporated into the resection blade together.

In other embodiment of the tissue excision and cutting apparatus, the resection blade further comprises a suction sampling collecting means which is detachably connected to the rear end of the hollow cylinder body for sucking and collecting a part of tissue cut off as a sample piece by the resection blade.

According to such a tissue excision and cutting apparatus, since the suction sampling collecting means sucks to collect by effecting active suction force instead of keeping airtight in the hollow cylinder body, the cut off tissue can be easily and sequentially suck and collected in the sampling collecting means.

In other embodiment of the tissue excision and cutting apparatus, a holding craw similar to thorn is provided in inner surface adjacent to the tip end of resection blade for preventing dropping out the tissue cut off as a sample piece by peripherally and partially holding it.

In the present invention, a forceps used together with the present apparatus has been also proposed, wherein the forceps comprises a clamp provided at a tip end of the forceps and having a movable jaw capable of opening and closing which is joined to a fixed jaw provided with a chopping block piece, an open-close mechanism with a hand operation part for opening and closing the movable jaw, and a longitudinal penetrating passage into which the resection blade is inserted and moves back and forth therein.

Such a forceps is the one used for the tissue excision and cutting apparatus of the present invention, and accordingly a part of tissue can be finely and surely cut off.

When such a forceps is used, any kinds of resection blade which are rotatable or not rotatable can be also employed and a chopping block piece may serve as the so called a cutting board.

According to other embodiment of the forceps, the operation part of the forceps is constructed such that it can be held by one hand and the movable jaw can be operated for opening and closing by manual operation of the one hand.

Further in another tissue excision and cutting apparatus of the present invention, the operation part of the forceps is constructed such that it can be held by one hand and the movable jaw can be operated by the one hand. Therefore, the apparatus is very convenient for handling because forceps can be held and manually operated by the same one hand while the resection blade can be operated by another hand.

Therefore, it is easy and convenient to handle such a forceps because it can be opened and closed and held the same one hand with another hand operating a resection blade.

Further in other embodiment of the present invention, a chopping block piece of the resection blade is formed with a blade receiving surface on which the whole circumference of the blade contacts.

According to such construction, a part of tissue grasping by the clamp can be sharply and finely cut off by pressing the blade of the resection blade onto the surface, by which a sample piece of tissue with a sharp cut end can be obtained.

Still another embodiment of the invention, a sealing mechanism for airtightly sealing the penetrating passage is further provided for isolating ventilation of the open air even when the forceps is inserted into the passage or is pulled out from the passage.

According to such construction, outer air is prevented from entering in abdominal cavity or the endo-bag through the penetrating passage and especially pneumoperitoneum gas is well prevented from leaking out when being filled in the endo-bag.

In other embodiment of the invention, the sealing valve mechanism is detachable and exchangeable for the penetrating passage.

Therefore, according to such construction, it is very useful for preventing contamination or contagion since it can be easily exchanged every time the forceps is used.

BRIEF DESCRIPTION OF DRAWINGS

These and other objects and advantages of the present invention will become clear from the following description with reference to the accompanying drawings, wherein:

FIG. 3($b$) is a partial cutaway front view when it is closed according to a tissue excision and cutting apparatus of the present invention.

FIG. 4($b$) is a vertical section after tissue is cut.

FIG. 5($a$) shows a vertical section when tissue is cut according to a tissue excision and cutting apparatus of the present invention.

FIG. 5($b$) shows a vertical section after tissue is cut according to a tissue excision and cutting apparatus of the present invention.

FIG. 12($b$) is a fragmental view in the direction of the arrow X according to a tissue excision and cutting apparatus of another embodiment of the present invention.

FIG. 13($b$) shows after it is loaded, and

FIG. 13($c$) shows when the resection blade or the rotatable resection blade is inserted according to a tissue excision and cutting apparatus of the present invention.

FIG. 14($a$) is its front view according to a tissue excision and cutting apparatus of the present invention.

FIG. 14($b$) is a partial vertical section according to a tissue excision and cutting apparatus of the present invention.

FIG. 16($a$) is its front view according to a tissue excision and cutting apparatus of the present invention.

FIG. 16($b$) is its partial vertical section according to a tissue excision and cutting apparatus of the present invention.

FIG. 19(a) to FIG. 19(f) explain operation of a suction and sampling means used for a resection blade or a rotatable resection blade of the present invention.

FIGS. 20(a), (b), (c) show one usage of a tissue excision and cutting apparatus and a forceps of the prior art.

FIG. 21(a) is a front view of a partial vertical section a tissue excision and cutting apparatus integrated with a forceps according to the prior art.

FIG. 21(b) is its rear view of a tissue excision and cutting apparatus integrated with a forceps according to the prior art.

DETAILED DESCRIPTION OF THE INVENTION

Figure 1:
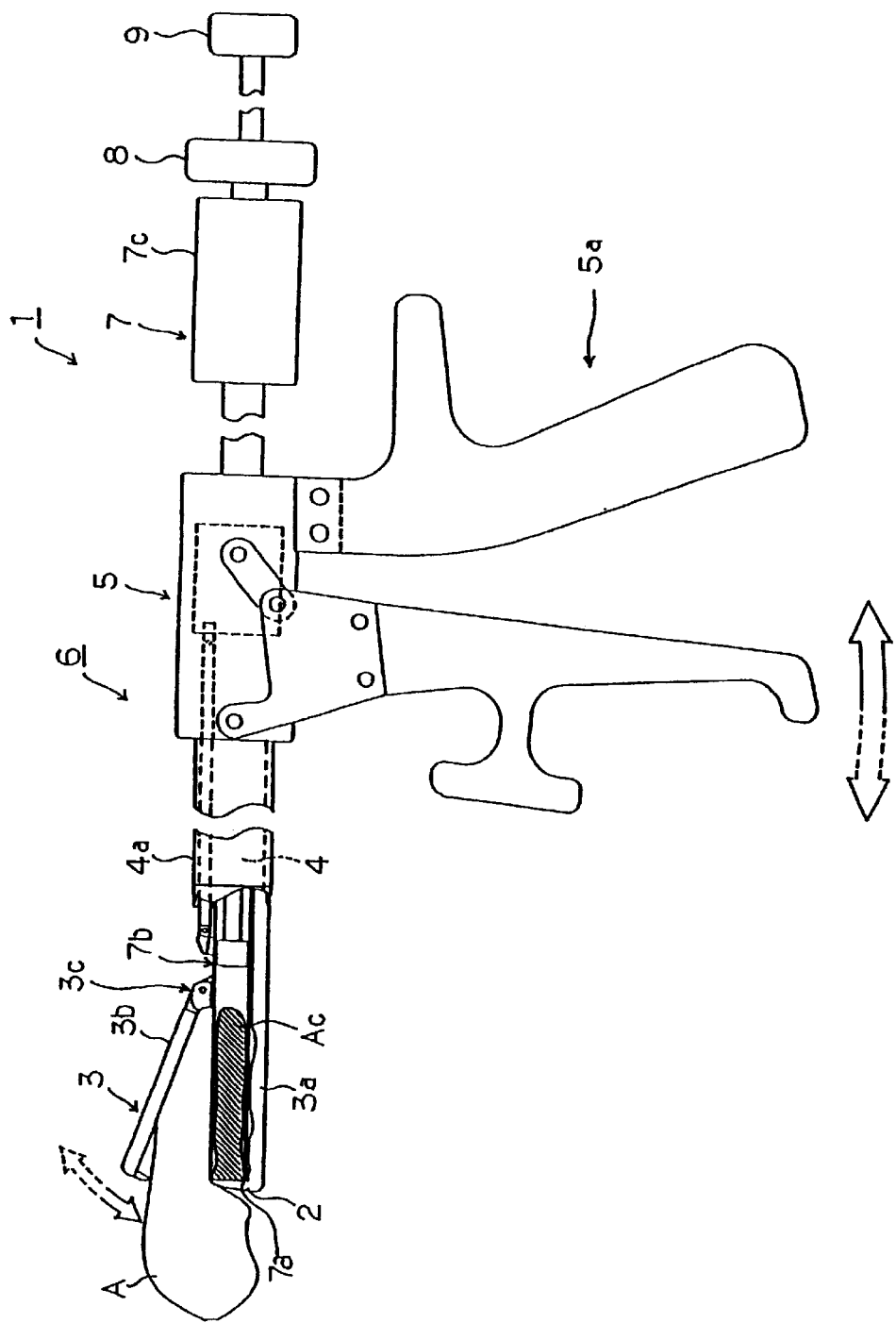
FIG. 1 is a partially cutaway front view showing one embodiment of a tissue excision and cutting apparatus of the present invention.

Now embodiments of tissue excision and cutting apparatus will be explained referring to the drawings.

FIG. 1 is a partially cutaway front view of one embodiment of a tissue excision and cutting apparatus of the present invention.

A tissue excision and cutting apparatus comprises a resection blade 7 having an inner hollow cylinder body formed with a cutting blade 7a at its tip end, and a forceps 6 for cutting off a part of tissue A as a sample piece.

The forceps 6 has a clamp 3 for grasping a part of tissue A in which the clamp has a movable jaw 3b capable of opening and closing joined to a fixed jaw 3a with a chopping block piece 2, an open-close mechanism 5 with an operation part 5a for opening and closing the movable jaw 3b, and a longitudinal penetrating passage 4 into which the resection blade 7 is inserted and moves back and forth therein.

The chopping block piece 2 is a characteristic of the tissue excision and cutting apparatus 1, is vertically provided at the fixed jaw 3a in such manner it intercepts the penetration passage 4 as a stopper of the resection blade 7 to be inserted into the longitudinal penetrating passage 4 for cutting tissue A, and works as so called a cutting board.

The fixed jaw 3a is provided normally at one end of a forceps cylinder 4a with the longitudinal penetrating passage 4 therein, and the movable jaw 3b is joined to the fixed jaw 3a by a hinge 3c so as to be pivotally opened and closed. The fixed jaw 3a, the movable jaw 3b and the hinge 3c construct the clamp 3. These parts will be detailed hereinafter.

The longitudinal penetrating passage 4 is constructed with a cylindrical body as the forceps cylinder 4a and the open-close mechanism 5, which will be also explained hereinafter, is provided in the forceps cylinder 4a and on the opposite side of the fixed jaw 3a in such a manner as to form the longitudinal penetrating passage 4. The operation part 5a for holding the tissue excision and cutting apparatus 1 by one hand and for opening and closing the movable jaw 3b is provided at a back end of the open and close mechanism 5 in such a manner that it directs approximately normally to the longitudinal direction of the forceps cylinder 4a.

The resection blade 7 is comprised of a cylinder body 7b formed with the cylindrical blade 7a at its one end and a holding portion 7c for holding the resection blade 7 at its periphery of the other end, and is so constructed as to contain cut off tissue as a sample piece Ac at its tip of the hollow cylinder.

At the back end of the resection blade is provided a sealing rod 8 for airtightly sealing the inner portion of hollow cylinder body and a push rod 9 for extruding the cut off tissue as a sample piece Ac by being airtightly inserted into the hollow cylinder body from a push hole (not shown) provided at the back end of the sealing rod 8.

The sealing rod 8 and the push rod 9 are detachable on the resection blade 7 if necessary and they will be explained hereinafter.

According to the tissue excision and cutting apparatus 1, tissue A can be grasped with a clamp 3 only by closing operation of the operation part 5a (solid line arrow in the figure) while holding the same part 5a by one hand. Under such a condition, inserting the resection blade 7 into the longitudinal penetrating passage 4 of the forceps 6 by another hand and bringing the blade 7a of the resection blade 7 into direct contact with the tissue A by pressing it or bringing the blade 7a of the resection blade into contact with the tissue A while twisting it right and left at its discretion, thereby cutting off the objective tissue A to obtain only a part of the objective tissue A as a sample piece Ac without damaging the surrounding tissues and with safety and sureness.

Namely, according to the tissue excision and cutting apparatus, since the chopping block piece 2 body provided at the tip of the fixed jaw 3a serves as a chopping board, only a part of the objective tissue A held by the clamp 3 can be safely and surely cut off comparing to the apparatus such a prior type that the tissue is cut off while being drawn into a cylinder of the resection blade 7.

Further, the clamp 3 can be opened and closed by manual operation of one hand while holding the tissue excision and cutting apparatus 1 by the one hand and thereby enabling to operate the resection blade 7 by the other hand. Therefore, the required operation for cutting off tissue can be done by one person so that such an apparatus is suitable for laparoscopic surgery or the like.

Figure 2:
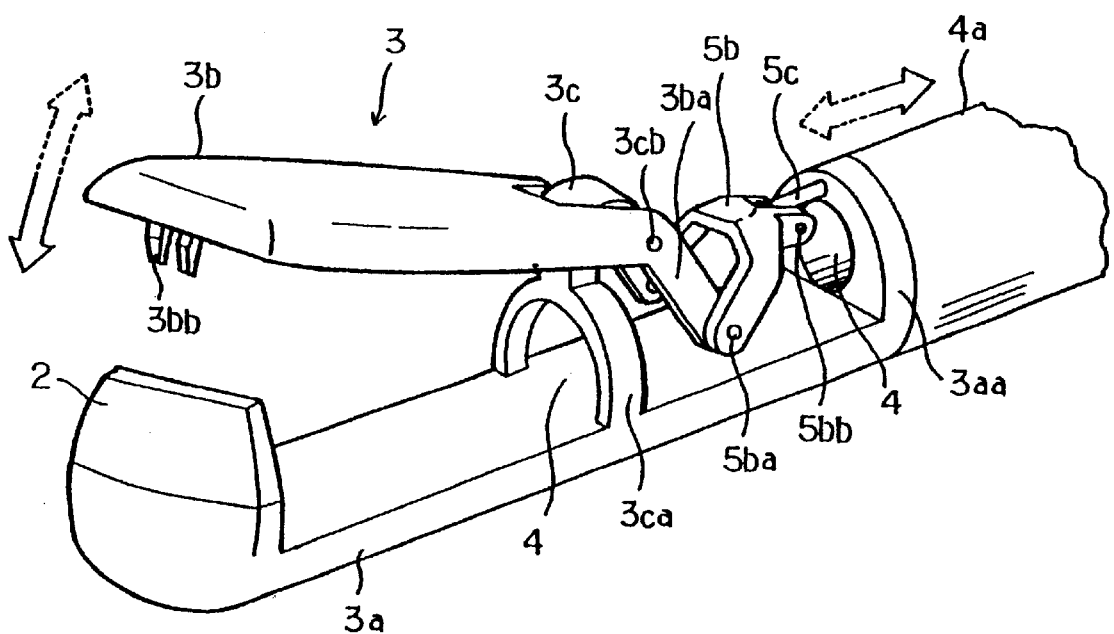
FIG. 2 is a perspective view of a clamp of a tissue excision and cutting apparatus of the present invention.

FIG. 2 is a perspective view of the clamp 3 of the tissue excision and cutting apparatus 1. The repetition explanation will be omitted by adding same reference numerals to the parts already explained hereinafter.

The clamp 3 is constructed such that the fixed jaw 3a is attached with the movable jaw 3b so as to be opened and closed and the movable jaw 3b is connected to the open-close mechanism 5 operated by the operation part 5a. The mechanism 5 is provided so as not to interrupt the blade 7a of the resection blade 7 forwarding to the chopping block piece 2, or the mechanism is provided in such manner as to assure the longitudinal penetrating passage 4.

The fixed jaw 3a is provided with an arch-like support body 3ca constructing a hinge 3c for supporting the movable jaw 3b so as to be opened and closed. An escape hole of this arch form constructs the longitudinal penetrating passage 4. A hinge hole (not shown) is provided at the upper projection of the support body 3ca, a hinge pin 3cb is inserted into the hole, and a hinge hole (not shown) provided at the open-close end of the movable jaw 3b is outwardly engaged into the hinge pin 3cb.

The support body 3ca and the hinge pin 3cb construct the hinge 3c and the movable jaw 3b can be rotate around the hinge pin 3cb as a rotation rod so as to be opened and closed for the fixed jaw 3a.

The attachment method of the movable jaw 3b on the fixed jaw 3a so as to be opened and close isn't limited to the above-mentioned one which uses a hinge supporting with one rod. Other method wherein the movable jaw 3b is connected to the fixed jaw 3a with plural arms so as to form a parallelogram and the movable jaw 3b is opened or closed always keeping parallel to the fixed jaw 3a may be used.

A link arm 3ba is extended from the open-close end of the movable jaw 3b so as to make a prescribed angle with the movable jaw 3b, and a link hole (not shown) is provided at its tip and rotatably connected to a link member 5b by a link pin 5ba. The link member 5b is further rotatably connected to a connecting rod 5c connecting the operation part 5a side and the clamp 3 side of the forceps cylinder 4a and is provided with the escape hole constructing the longitudinal penetrating passage 4.

A hook 3bb for preventing moving of the tissue to be held by biting into the tissue is provided at the tip opposite to the link arm 3ba side of the movable jaw 3b facing to the fixed jaw 3a, however such a 3bb hook isn't inevitable.

According to such a clamp 3 constructed mentioned above, the movable jaw 3b is closed (a solid line arrow) when the connecting rod 5c is moved rear (into a solid line arrow), the movable jaw 3b is opened (a broken line arrow) when the connecting rod 5c is moved near (into a broken line arrow).

Any of them are provided so as to assure the longitudinal penetrating passage 4 for forwarding the resection blade 7 to be attached with the chopping block piece 2 provided at the tip of the fixed jaw 3a without being an obstacle. Further, the longitudinal penetrating passage 4 may assure insertion of the resection blade 7 and may be provided with an open end as mentioned above other than the forceps cylinder 4a which is closed perpendicular to the longitudinal direction.

A connection 3aa is vertically connected with the fixed jaw 3a, connects the forceps cylinder 4a and the fixed jaw 3a, and is provided with a support hole for inserting the connecting rod 5c slidably.

Figure 3:
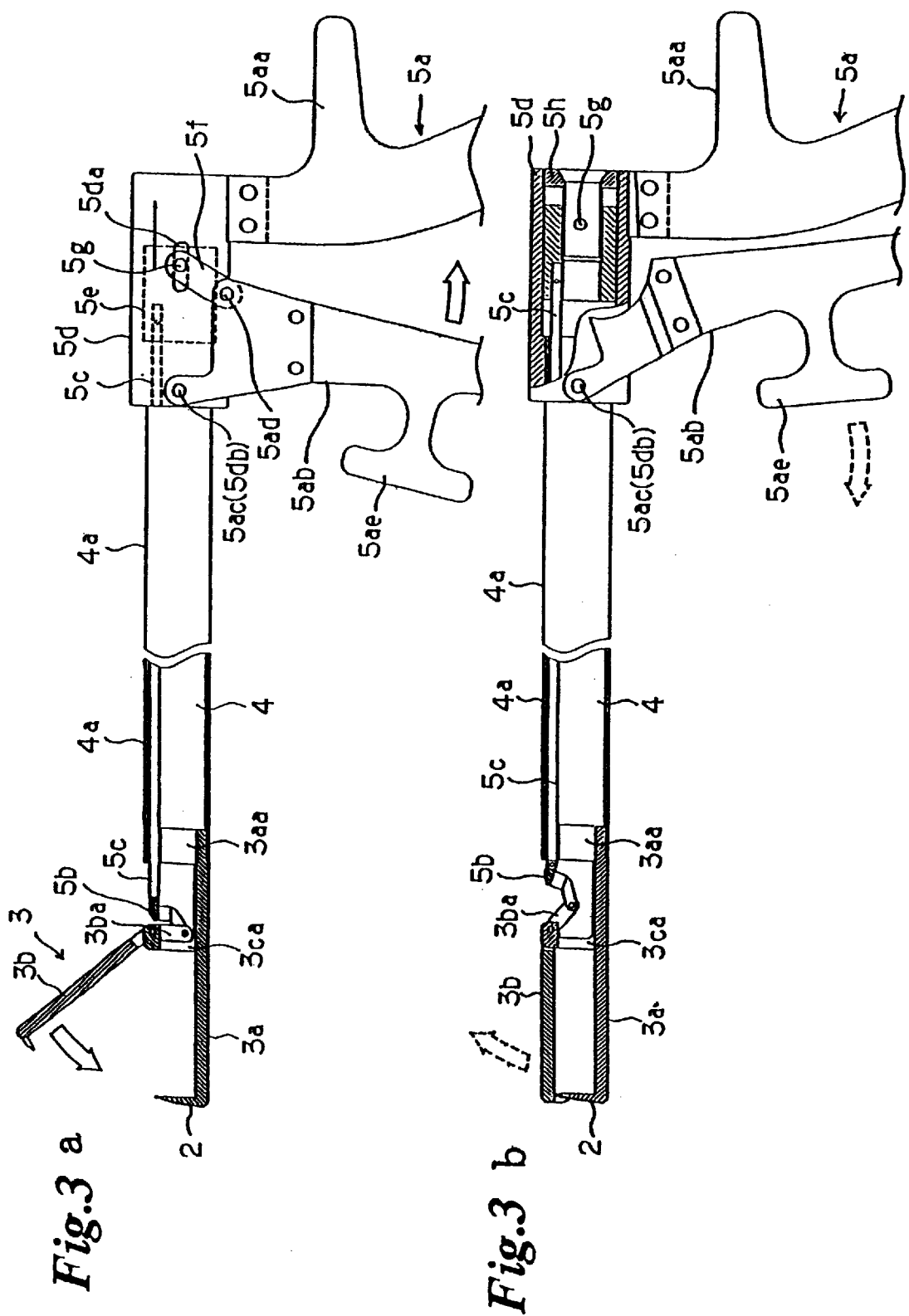
FIG. 3($a$) is a partial cutaway front view when the clamp is opened according to a tissue excision and cutting apparatus of the present invention.

FIG. 3 shows performance of the operation part 5a and the open-close mechanism 5 of the tissue excision and cutting apparatus 1 of the present invention. FIG. 3(a) is a partial cutaway front view when the clamp 3 is opened and FIG. 3(b) is a partial cutaway front view when it is closed.

The connecting rod 5c passes through the connection 3aa and the upper part of the forceps cylinder 4a assuring the longitudinal penetrating passage 4, extends to the operation part 5a side of the forceps cylinder 4a, and is connected to a slide block 5e.

The slide block 5e is contained in an operating mechanism case 5d slidably fixed at the operation part 5a side of the forceps cylinder 4a and the back and forth movement of the slide block 5e is transmitted to the clamp 3 side of the forceps cylinder 4a via the connecting rod 5c so that the link member 5b is moved back and forth. The slide block 5e is provided with a pair of link pins 5f at both ends of peripheral and a pair of link plates 5e connecting the operation part 5a and the slide block 5e are outwardly inserted into the link pins 5g so as to be slidable. A slide long hole 5da working as a guide of moving of the link pins 5g accompanying with back and forth movement of the slide block 5e is provided at a position corresponding to the link pins 5g of the operation mechanism case 5d so as to allow back and forth sliding of the slide block 5e and prevent rotation of the slide block 5e.

A pair of link support pins 5db are provided forward the operation mechanism case 5d and a rear cover 5h is provided at back end of the case 5d.

The operation part 5a is comprised of a fixed operation part 5aa fixedly provided for the operation mechanism case 5d and a movable operation part 5ab which can be opened or closed by rotating the link support pins 5db of the case 5d as a rotating rod against the fixed operation part 5aa. Such rotation is accomplished by that a link support hole 5ac provided for the movable operation part 5ab is outwardly inserted in the pins 5db of the case 5d. A link support 5ad associating to a link plate 5f outwardly inserted in the link pins 5g of the slide block 5e and a finger stopper 5ae for acting operating force offingers in both open and close directions are provided for the movable operation part 5ab.

A link mechanism is constructed by the link pins 5g of the slide block 5e sliding back and forth in the operation mechanism case 5d, the link plate 5f, the link support 5ad and the link support hole 5ac of the removable operation part 5ab, and the link support pin 5db of the case 5d. When the movable operation part 5ab of the operation part 5a is opened or closed by such a link mechanism, the movable jaw 3b of the clamp 3 can be opened or closed.

When the fixed operation part 5aa of the operation part 5a is held by one hand as shown in FIG. 3(a) and a first finger and a long finger (they are called "operation fingers") are operated into closing direction (a solid line arrow in the figure) so as to clip the finger stopper 5ae, the slide block 5e goes back, such a movement is transferred to the link member 5b by means of the connecting rod 5c, the link arm 3ba of the clamp 3 is rotated, and the movable jaw 3b is moved into closing direction (a solid line arrow in the figure).

On the other hand, when the operation fingers are operated into open direction (a broken line arrow in the figure) as shown in FIG. 3(b), the movement is transmitted to the link member 5b by the connecting rod 5c, the link arm 3ba of the clamp 3 is rotated opposite direction, and the movable jaw 3b is moved into opening direction (a broken line arrow in the figure).

Accordingly the clamp 3 can be easily opened and closed by operating the operation part 5a by one hand.

Of course an escape for providing the longitudinal penetrating passage 4 is formed at inside of any of the forceps cylinder 4a, the slide block 5e, attachment part of the link pins 5g of the slide block 5e, and the rear cover 5h so that the resection blade 7 or the rotary blade, will be described hereinafter, can be inserted.

Figure 4:
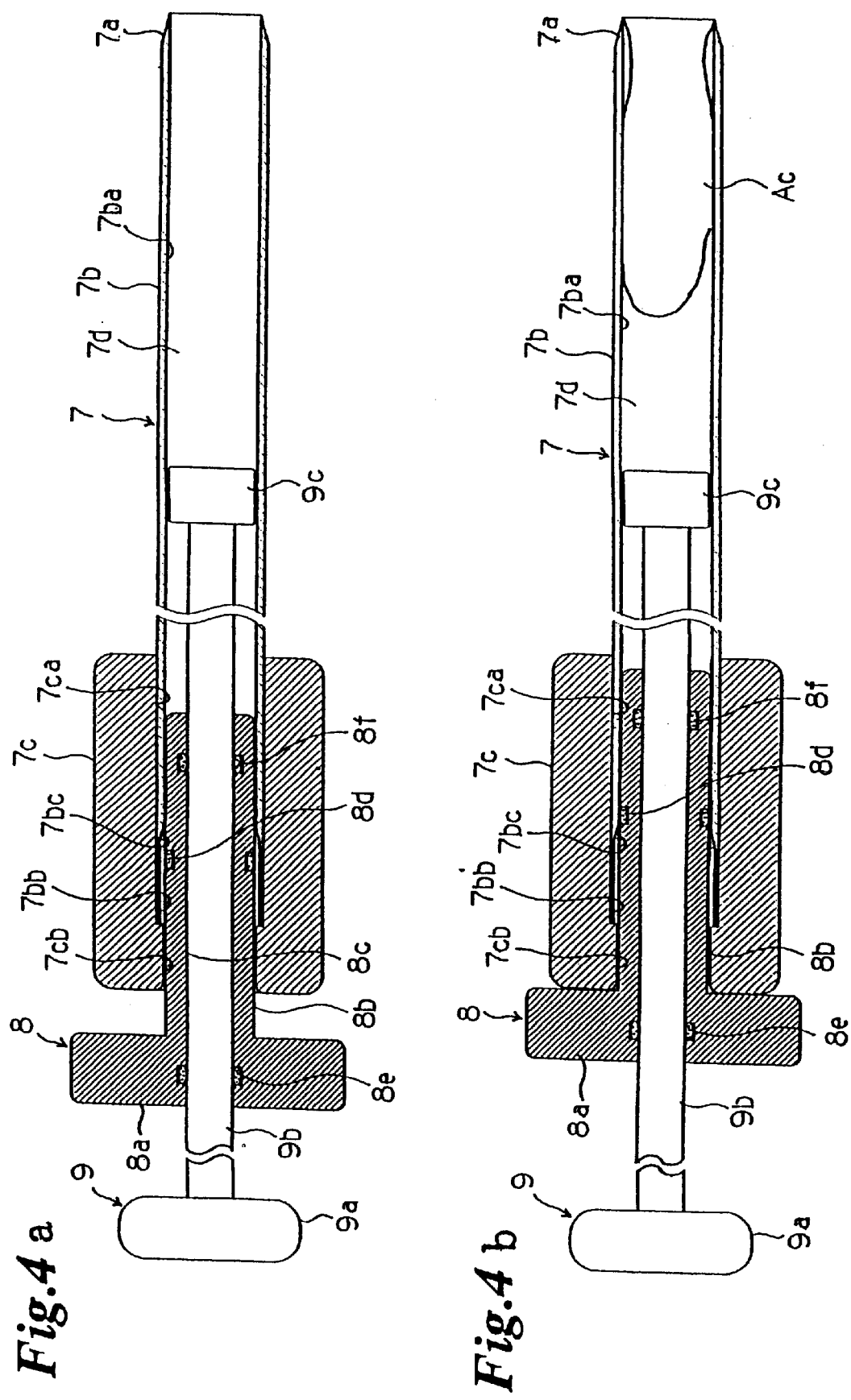
FIG. 4($a$) is a vertical section when tissue is cut.
Figure 6:
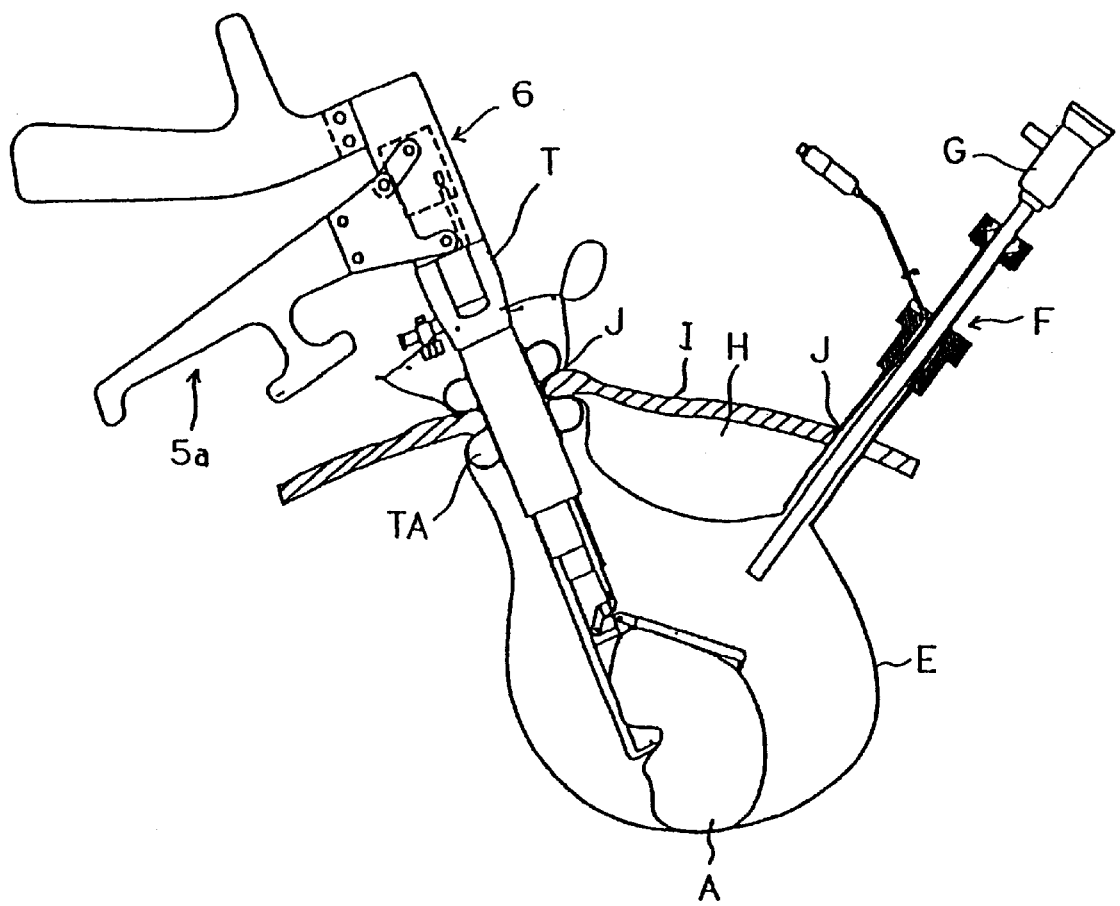
FIG. 6 is an explanatory view showing sampling procedure 1 for tissue sample by means of the tissue excision and cutting apparatus of the present invention.
Figure 7:
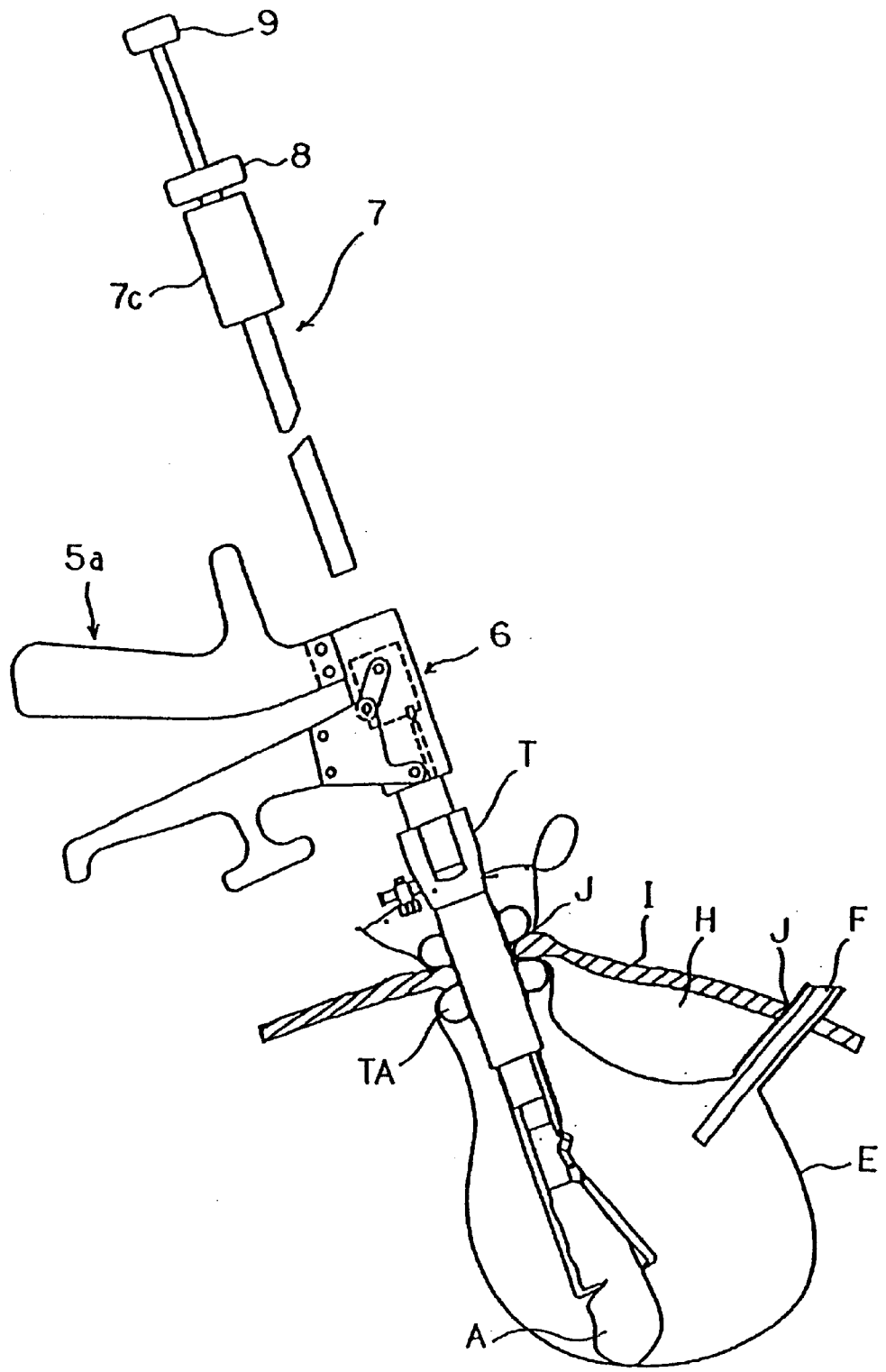
FIG. 7 is an explanatory view showing sampling procedure 2 for tissue sample by means of the tissue excision and cutting apparatus of the present invention.
Figure 8:
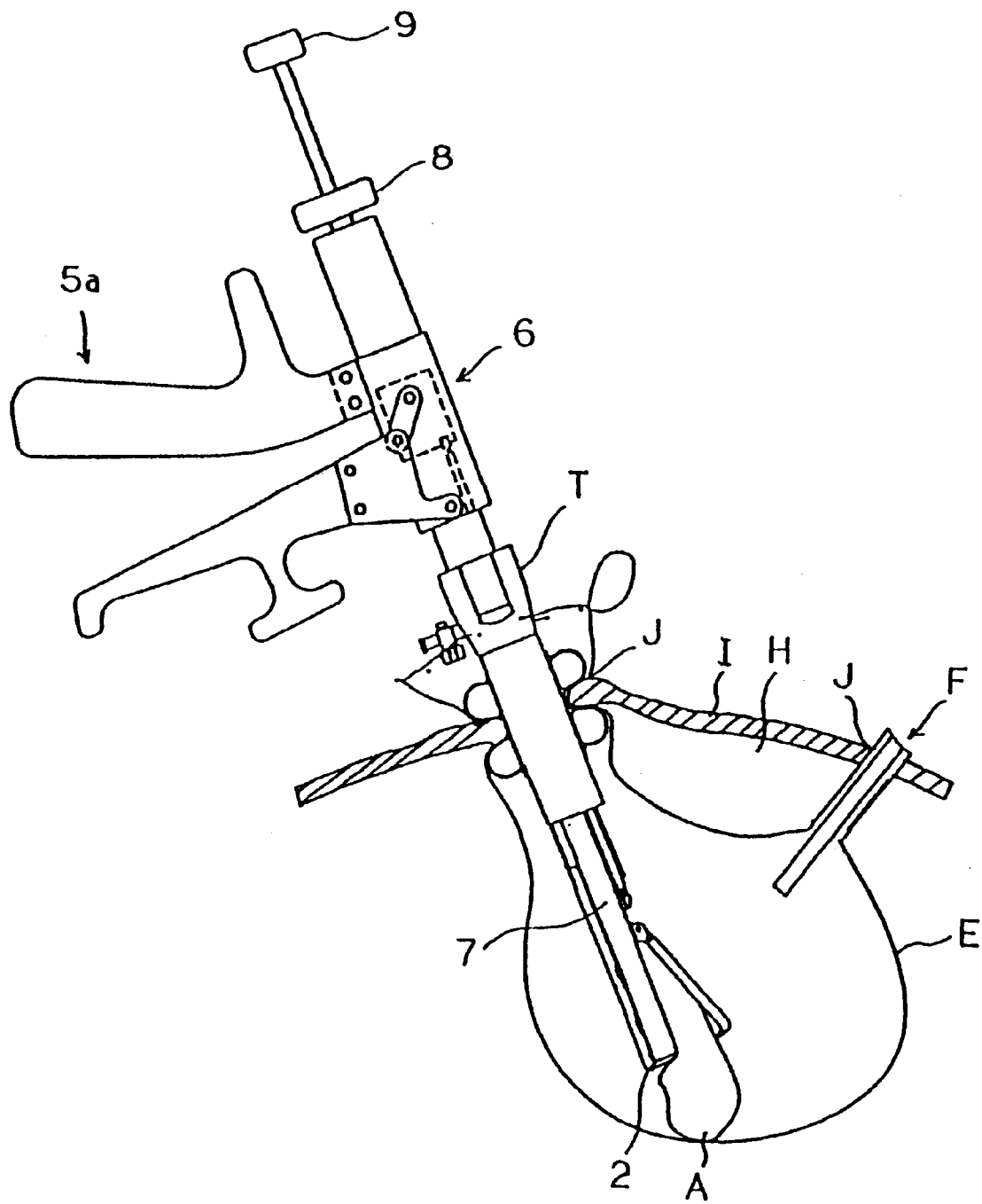
FIG. 8 is an explanatory view showing sampling procedure 3 for tissue sample by means of the tissue excision and cutting apparatus of the present invention.
Figure 9:
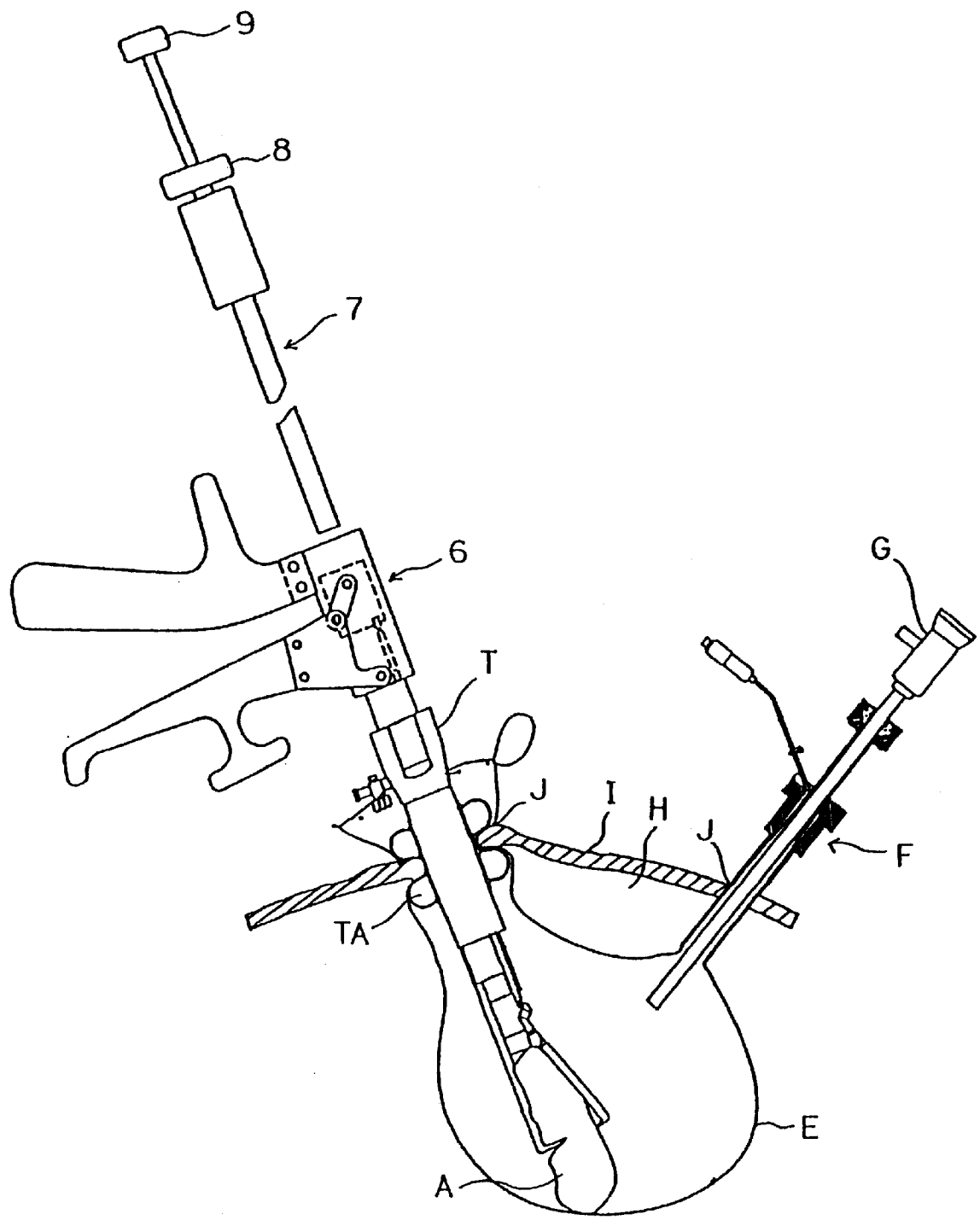
FIG. 9 is an explanatory view showing sampling procedure 4 for tissue sample by means of the tissue excision and cutting apparatus of the present invention.
Figure 10:
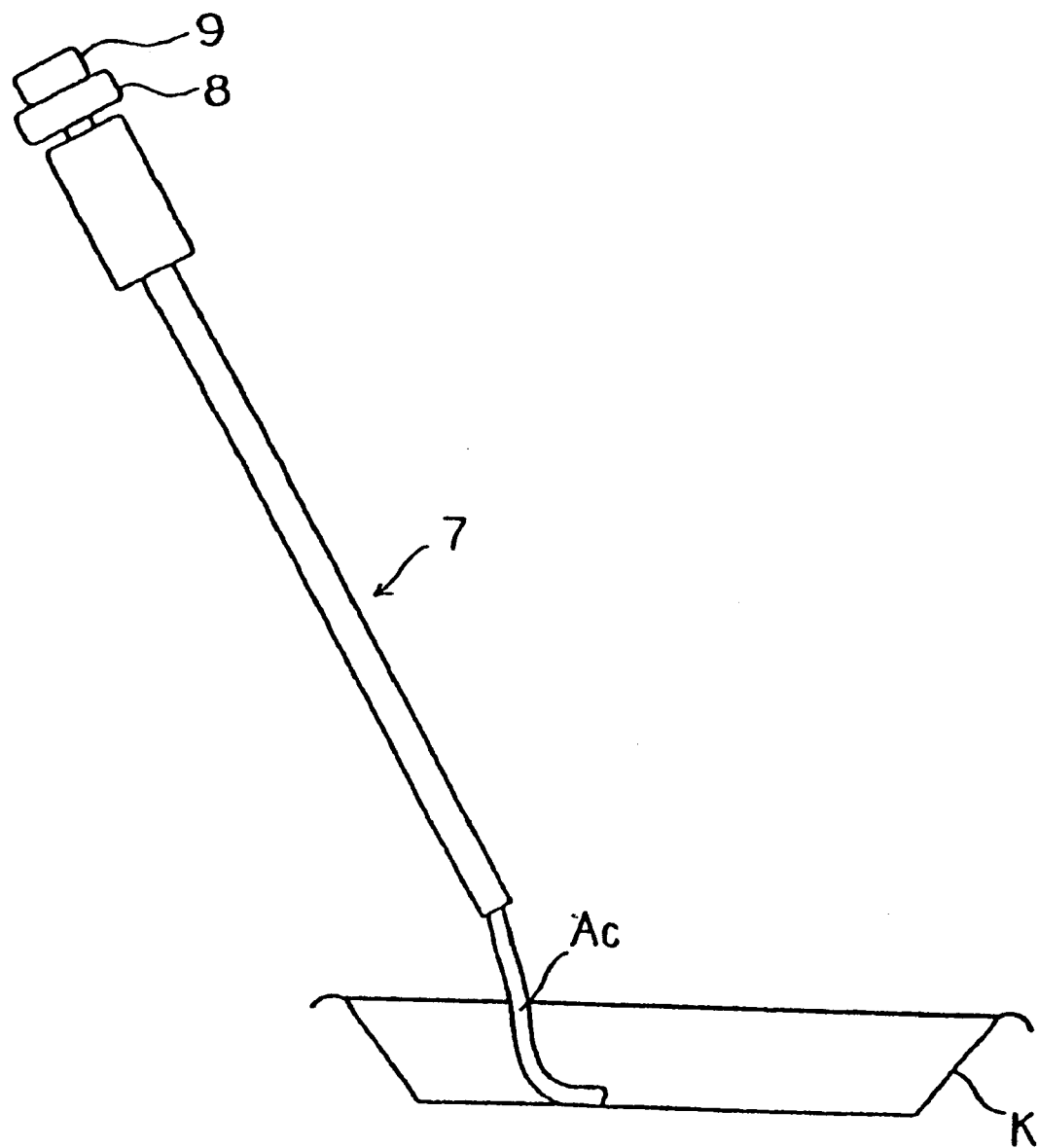
FIG. 10 is an explanatory view showing sampling procedure 5 for tissue sample by means of the tissue excision and cutting apparatus of the present invention.

FIG. 4 shows operation of one embodiment of a sealing rod and a push rod provided for the resection blade or the rotatable resection blade of the present invention. FIG. 4(a) is a vertical section when tissue is cut and FIG. 4(b) is a vertical section after tissue is cut.

Now detailed construction of the resection blade 7 provided corresponding to the sealing function of the seal rod 8.

The resection blade 7 is constructed such that the rear end of the hollow and cylindrical main body 7b provided with the blade 7a at its tip is inserted in the hollow and cylindrical holding portion 7c.

The inner diameter of the main body 7b isn't uniform. The main body 7b is comprised of a standard inner diameter part 7ba having the same inner diameter as the blade 7a portion and an escape inner diameter part 7bb having the inner diameter larger than the standard inner diameter part 7ba. The standard inner diameter part 7ba occupies almost the inside of the main body 7b from the tip with the blade 7a to the rear end and the escape inner diameter part 7bb occupies only at a fixed distance from the rear end. These two inner diameter parts 7ba and 7bb are connected by a gently tapered part 7bc.

The inner diameter of the holding portion 7c is tiered and comprised of an inserting hole 7ca for tightly inserting the rear end of the main body 7b and a guide hole 7cb of which inner diameter is smaller than that of the inserting hole 7ca and also is the same as or a little larger than the standard inner diameter part 7ba of the main body 7b. The resection blade 7 is constructed such that the rear end of the main body 7b is inserted in the inserting hole 7ca of the holding part 7c so as to bump into the tiered portion of the inserting hole 7ca and the guide hole 7cb.

According to such a resection blade 7, the resection blade 7 can be held by the holding part 7c and also sealing function of the sealing rod 8 can be brought out effectively as mentioned herein.

The sealing rod 8 is inserted in the guide hole 7cb of the holding part 7c from the rear end of the resection blade 7 and is provided with an rod part 8b having a little smaller external diameter than the inner diameter of the standard inner part 7ba of the main body 7b and a rib 8a contacting the rear end of the holding part 7c. And the center of the sealing rod 8 is formed with a push hole 8c for airtightly inserting the push rod 9 along the axial direction.

An O-ring 8d is provided at an appropriate portion of the external diameter of the rod part 8b and has an sealing effect for the standard inner diameter part 7ba and doesn't have an sealing effect for the escape inner diameter part 7bb. Namely the external diameter of the O-ring 8d is larger than the inner diameter of the standard inner diameter part 7ba and smaller than the inner diameter of the escape inner diameter part 7bb.

Therefore, the O-ring 8d is positioned in the escape inner diameter part 7bb of the main body 7b and sealing function between the O-ring 8d and the escape inner diameter port 7bb doesn't achieved in FIG. 4(a). So, air in a hollow part 7d in the resection blade 7 is allowed to be communicated outside from the sealing rod 8 side via the space between the standard inner diameter part 7ba and a head 9c of the push shaft 9, the space between the standard inner diameter 7ba, the escape inner diameter part 7bb, the guide hole 7cb of the holding portion 7c and the rod part 8b of the sealing rod 8. Under such a condition, the resection blade 7 is pressed on the tissue so that the tissue sample Ac is taken in the hollow part 7d of the resection blade 7 (see FIG. 4(b)).

On the other hand when the sealing rod 8 is fully pushed into the resection blade 7 as shown in FIG. 4(b), the O-ring 8d is positioned in the standard inner diameter part 7ba of the main body 7b so that air in the hollow part 7d of the resection blade 7 is sealed not to communicate outside from the sealing rod 8 side. When the O-ring 8d moves to the standard inner diameter part 7ba from the escape inner diameter part 7bb, it isn't damaged because it moves in the gently tapered part 7bc.

When such a sealing is accomplished, the hollow part 7d of the resection blade 7 is covered with the tissue sample Ac at its tip so that the tissue sample Ac doesn't easily dropped off the resection blade 7 because negative pressure is applied on the hollow part 7d when the sample Ac is going to be dropped from the resection blade 7.

O-rings 8e, 8f are provided for the forward and rear parts of the push hole 8c penetrating the center of the rod part 8b and the rib 8a so that the push rod 9 can move back and forth while keeping airtight between the push hole 8c and the rod portion 9b of the push rod 9 inserted therein.

The push rod 9 is comprised of the rod portion 9b and a rib 9a provided at its rear end and the head 9c provided at its forward end. The external diameter of the head 9c is a little smaller than the inner diameter of the hollow cylinder of the resection blade 7. The head 9c is detachable for the rod portion 9b by an appropriate association means such as a screw and can be disassembled so that the push rod 9 is removed from the sealing rod 8 in case of sterilization.

When cutting tissue, the sealing shaft 8 is inserted into the position where the O-ring 8d of the sealing rod 8 allows communication with outside air and the push rod 9 is set at the position where enough space for containing the tissue to be cut is remained at the tip of the head 9c.

In such a case, when the tissue A is grasped by the clamp 3 and is cut by the blade 7a by forwarding the resection blade 7, air can be leaked from the sealing rod 8 side even if the hollow cylinder of the resection blade 7 is covered with the cut tissue sample Ac and sealed airtightly as explained about FIG. 1. Therefore, cutting operation of tissue can't be hindered. And the rear end of the resection blade 7 is inserted by the sealing rod 8 so that leakage of waste such as body fluid and blood in abdominal cavity along the hollow cylinder of the resection blade 7 into outside is reduced.

After cutting tissue, the sealing rod 8 is pushed in the resection blade 7 at the position where the O-ring 8d of the sealing rod 8 keeps airtight and the push shaft 9 is remained at it is, as shown in FIG. 4(b).

Under such a condition, the inside of the resection blade 7 is kept airtight by the tissue sample Ac, the O-ring 8d of the sealing rod 8, and the O-rings 8e, 8f of the push rod 9 as mentioned above. When the resection blade 7 is retracted from the forceps 6 while containing the cut and obtained tissue sample Ac at its tip and is moved to a prepared sample tray with the contained side downward, the contained tissue sample Ac doesn't dropped from the resection blade 7 because of atmospheric pressure.

After the resection blade 7 reaches the prepared sample tray, the sealing rod 8 is positioned like FIG. 4(a) and the contained tissue sample Ac is extruded by pushing the push rod 9.

Accordingly the tissue A can be surely cut and the cut and sampled tissue sample Ac can be collected safely and certainly.

FIG. 5 shows operation of another embodiment of a sealing rod and a push rod used for a resection blade or a rotating resection blade of the present invention. FIG. 5(a) shows a vertical section when tissue is cut and FIG. 5(b) shows a vertical section after tissue is cut.

A push shaft 11 has both functions of the sealing rod 8 and the push rod 9 in FIG. 4 and a sealing rod 10 only has an auxiliary function to seal or allow communication with outside air.

The shape of the push rod 11 is almost the same as the push rod 9 in FIG. 4 and is comprised of a rib 11a, an rod part 11b and a head 11c. Differently, an O-ring lid for keeping airtight with the inner diameter of the hollow cylinder of the resection blade 7 is provided for the head 11c and an air vent hole 11e penetrating the center of the push rod 11 is provided.

The sealing rod 10 is used for sealing the air vent hole lie of the push rod 11.

When cutting tissue (FIG. 5(a)), only the push rod 11 is inserted into the resection blade 7 and the push rod 11 is set at the position where enough space for containing the cut tissue is obtained at the tip of the head 11c. The air vent hole 11e isn't sealed so that tissue can be preferably cut as mentioned above.

When the sealing rod 10 is inserted in the air vent hole 11e of the push rod 11 after cutting tissue (FIG. 5(b)), the air vent hole 11e is sealed so that the cut and sampled tissue sample Ac doesn't drop from the contained portion even if the resection blade 7 is extracted and moved as explained for FIG. 4(b). When the push shaft 11 is further pushed after being moved at a predetermined position, the tissue sample Ac is extruded from the tip of the resection blade 7 by air pressure between the tissue sample Ac and the head 11c of the push rod 11 which are kept airtight.

In such a case the tissue A can be surely cut and the cut and sampled tissue sample Ac can be collected safely and certainly.

If the construction members of the above-mentioned clamp 3 comprised of the chopping block piece 2, the fixed jaw 3a, and the movable jaw 3b, the forceps cylinder 4a having the penetrating passage 4, the open-close mechanism 5, the operation part 5a and the resection blade 7 are made of material excellent for sterilization and chemical proof, they are appropriate for surgical instruments because they can be easily sterilized such as autoclave sterilization after used. For example, the clamp 3, the forceps cylinder 4a, members of the open-close mechanism 5, and the resection blade 7 are preferably made of stainless steel and the O-ring for sealing is made of silicon rubber.

Next, one embodiment of actual procedures for sampling tissue sample using a tissue excision and cutting apparatus of the present invention in case of laparoscopic surgery will be explained.

FIG. 6 to FIG. 10 explain the procedure at five stages.

At the step 1 (FIG. 6), an inserting instrument F for inserting an endo-bag E in abdominal cavity H and a trocar T are set at a trocar site J of patient's abdomen I. In the figure, the endo-bag E is already inserted in the abdominal cavity H by the inserting instrument F, is expanded and contains the extracted organ A, an opening of the endo bag E is taken out of the trocar site F, the trocar T is inserted into the trocar site J, sterilized distilled water is injected into a trocar cuff TA provided for the trocar T so as to be expanded, and sealing between the trocar site J and the trocar T is kept.

On the other hand, the auxiliary opening for the endo-bag E is set at the inserting instrument F and a laparoscope G is inserted in the auxiliary opening so as to observe inside of the endo-bag E.

At first the forceps 6 is inserted into the trocar T and the organ A is grasped by operating the operation part 5a of the forceps 6 while confirming the position of the organ A by the laparoscope G.

At the step 2 (FIG. 7), the resection blade 7 is inserted into the longitudinal penetrating passage 4 of the forceps 6. In this time, the forceps 6 is held by one hand while grasping the organ A and the resection blade 7 can be easily inserted by holding the holding portion 7c by another hand. The sealing rod 8 with the push rod 9 is prepared for the resection blade 7 in such a manner that the resection blade 7 is allowed to be communicated with the air from the sealing rod 8 as shown in FIG. 4(a).

At the step 3 (FIG. 8), the tissue which is grasped by the clamp 3 and received by the chopping block piece 2 is finely and surely cut while the resection blade 7 is rotated right or left by a hand if necessary. The cut end is pressed and cut by the blade 7a of the resection blade 7 and the chopping block piece 2 or is sheared and cut by the blade 7a and a receiving blade (not shown) provided at the chopping block piece 2 depending on the shape of the blade 7a. The resection blade 7 is guarded with the clamp 3 so that tissue can be safely cut without damaging the endo-bag E by the blade 7a of the resection blade 7 is extruded.

At the step 4 (FIG. 9), the sealing rod 8 is fully inserted in the resection blade 7 and the resection blade 7 is extracted from the forceps 6 while sealing the hollow cylinder containing the cut tissue sample Ac.

At the step 5 (FIG. 10), the extracted resection blade 7 is moved to a sample tray K, the position of the sealing rod 8 is returned to where communication with outside air is allowed, then the tissue sample Ac contained at the tip in the hollow cylinder of the resection blade 7.

Accordingly, the tissue can be surely cut and the sampled tissue sample can be certainly moved to a prepared position.

Such an organ for cutting and sampling tissue thereof is generally attacked by malignant in many cases so that it is highly required to prevent that a part of the organ is leaked out of the endo-bag E, the endo-bag E itself is damaged, or the other normal organ is damaged or broken. According to the present invention, the blade 7a is constructed so as not to go forward the chopping block piece 2 so that such a danger isn't caused.

When the forceps of the present invention is used together with a rotatable resection blade which rotates automatically, its effect is further brought out.

Figure 11:
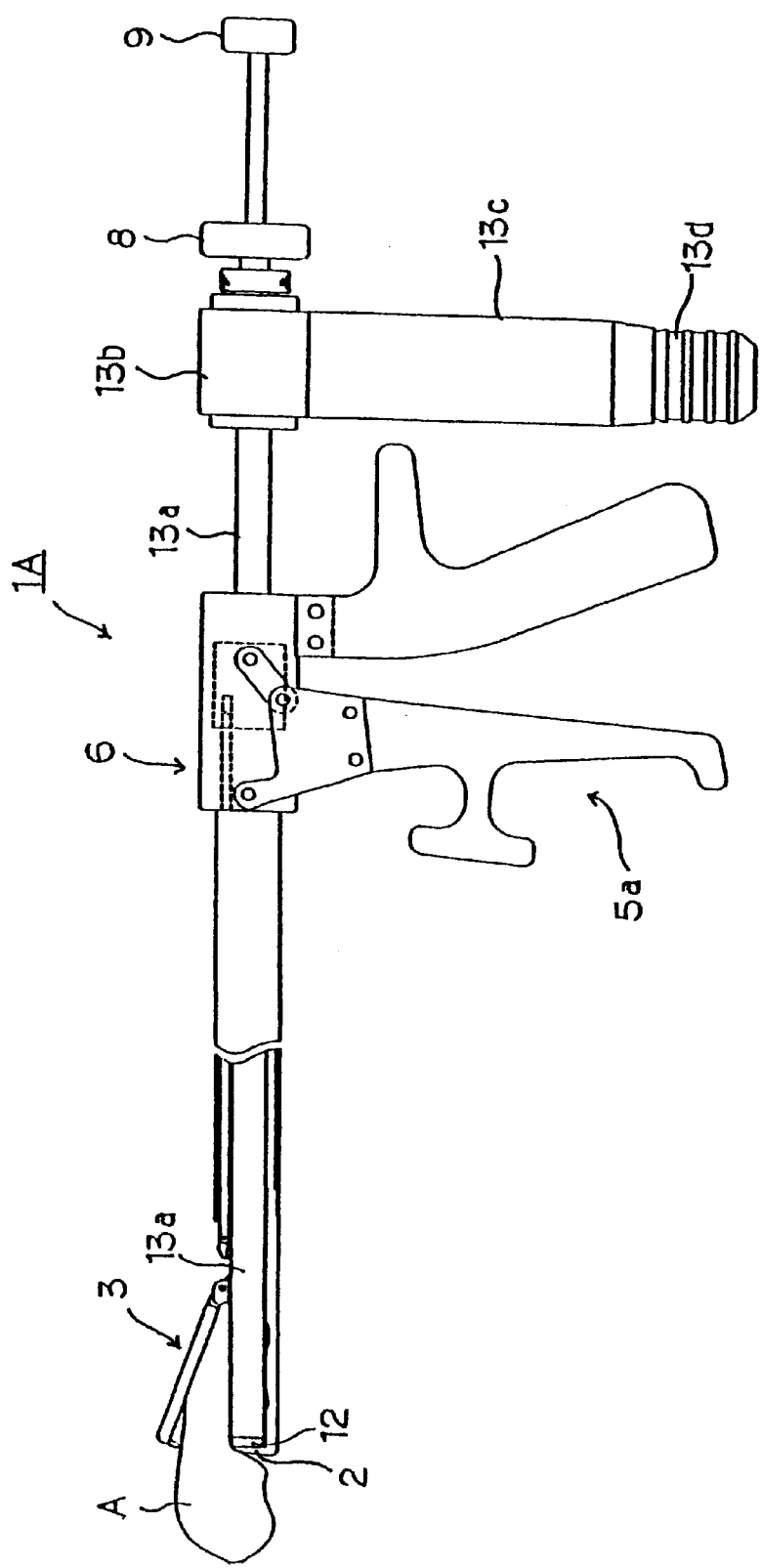
FIG. 11 is a partial cutaway front view showing one embodiment of a tissue excision and cutting apparatus of the present invention combined with a rotatable resection blade.

FIG. 11 is a partial cutaway front view showing one embodiment of the forceps of the present invention combined with the rotatable resection blade.

A tissue excision and cutting apparatus 1A is different from the apparatus 1 in that a resection blade is a rotatable resection blade 12. The rotatable resection blade 12 includes a guide cylinder 13a containing the rotatable resection blade 12 rotatably, a warm mechanism 13b with a warm and a warm wheel for driving and rotating the resection blade 12, and a driving and rotating mechanism 13 containing a mechanism for transmitting rotating power to the warm mechanism 13b and comprised of a transmission part 13c which can be a holding part of the resection blade 12 and a motor 13d as a drive source.

The driving and rotating mechanism 13 is provided with a controller such as a foot controller (not shown) for controlling on or off of driving and its rotation number so that rotation of the rotatable resection blade 12 can be controlled freely while operating the forceps 6 by one hand and grasping a transmission part 13c of the blade 12 by another hand.

Therefore, according to the tissue excision and cutting apparatus 1A, the tissue A which is grasped by the clamp 3 and received by the chopping block piece 2 like a cutting board can be finely cut.

The warm mechanism 13b is shown as one sample of the transmission mechanism for transmitting the rotational movement into perpendicular direction and the present invention isn't limited by such a warm mechanism 13b. For example, a mechanism combined with a bevel wheel may be used if the rotational movement is transmitted perpendicular. The driving and rotating mechanism 13 isn't limited to the above-mentioned one if the hollow cylindrical part is assured in the resection blade. For example, a direct drive electric motor comprising the rotary blade itself as a rotor thereof may be used and in such a case the above-mentioned warm mechanism isn't required.

The resection blade which is used together with the forceps comprising the tissue excision and cutting apparatus of the present invention may be rotated or not rotated. Further any resection blade can be combined if the cutting board function of the chopping block piece of the resection blade can be effectively utilized. Therefore, the forceps alone is available for a resection forceps 6A (FIG. 1) and in such a case it can execute cutting operation more finely and surely cooperating with the combined resection blade.

The chopping block piece and the sealing mechanism of the forceps, a drop-out prevention means and a suction means provided for the resection blade as an active means for preventing drop out of the tissue sample after sampled, which are other characteristics of the tissue excision and cutting apparatus of the present invention, will be explained hereinafter.

Figure 12:
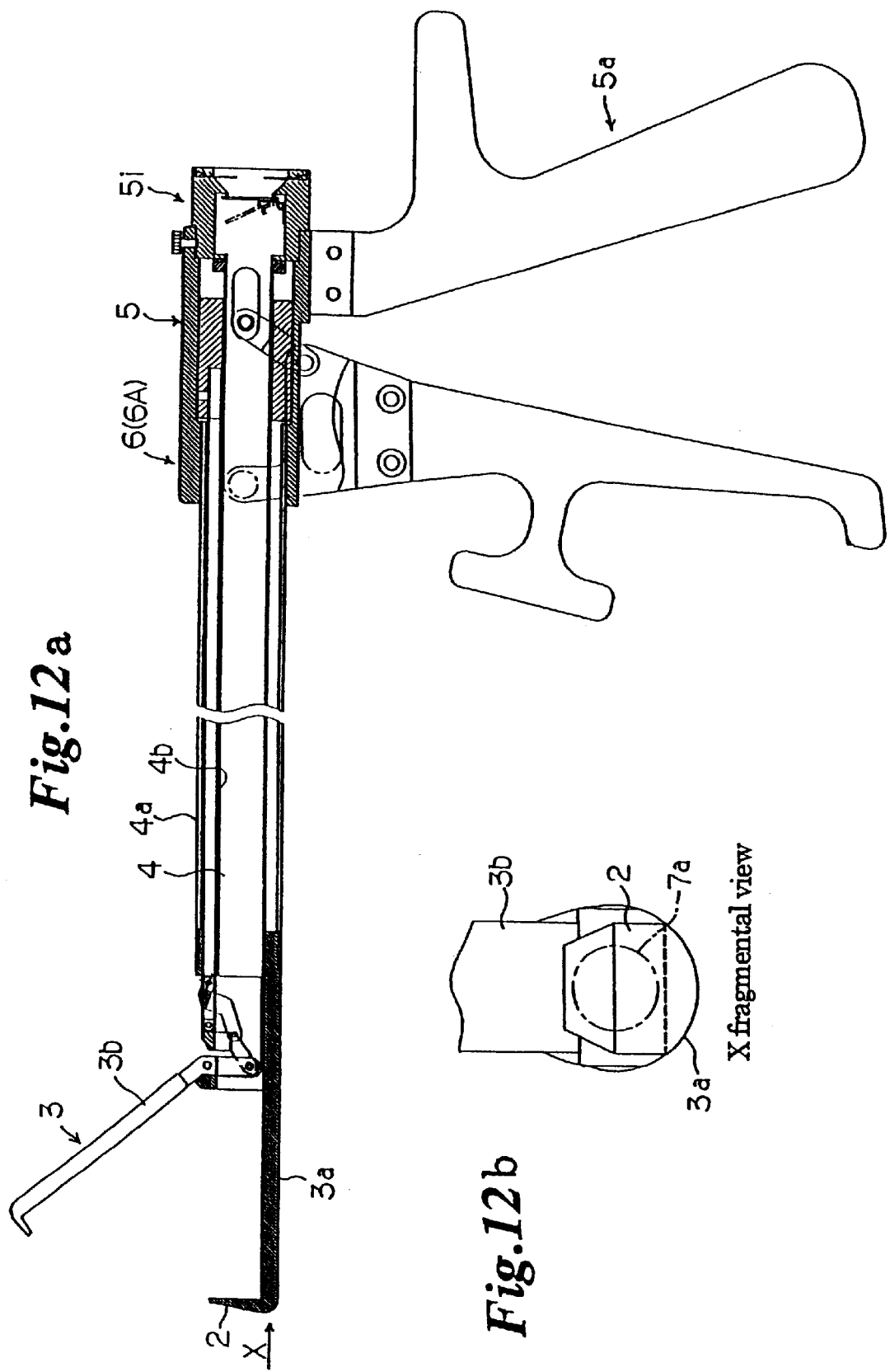
FIG. 12($a$) is a front view of a partial vertical section according to a tissue excision and cutting apparatus of another embodiment of the present invention.

FIG. 12 shows another embodiment of the forceps of the tissue excision and cutting apparatus of the present invention. FIG. 12(a) is a front view of a partial vertical section and FIG. 12(b) is a fragmental view in the direction of the arrow X.

At first FIG. 12(b) is explained. In this figure, the resection blade which is contacted with the chopping block piece 2 or the blade 7a of the rotatable resection blade is virtually shown by dotted lines.

The forceps 6 is constructed such that the size of the chopping block piece 2 provided at the tip of the fixed jaw 3 is designed to be contacted with the whole circumference of the blade 7a of the resection blade or the rotatable resection blade which is inserted in the longitudinal penetrating passage 4 of the forceps 6, as shown in the figure. Therefore, the chopping block piece 2 can be effected as a cutting board for any parts of the blade 7a and cutting end of tissue can be completely done so that the tissue sample can be completely cut and separated.

It isn't required to rip down the cut end by pulling the cut tissue sample with the forceps which has been done in the prior art. Therefore, tissue sample can be cut and sampled finely.

The virtual lines of the blade 7a almost correspond to the shape of the longitudinal penetrating passage 4 and the above-mentioned effect can be expected for the resection blade or the rotatable resection blade which can be inserted in the penetration passage 4.

Then the front view of the FIG. 12(a) will be explained. As shown in the figure, the forceps 6 is detachably provided with a sealing mechanism 5i at the end of the open-close mechanism 5.

Figure 13:
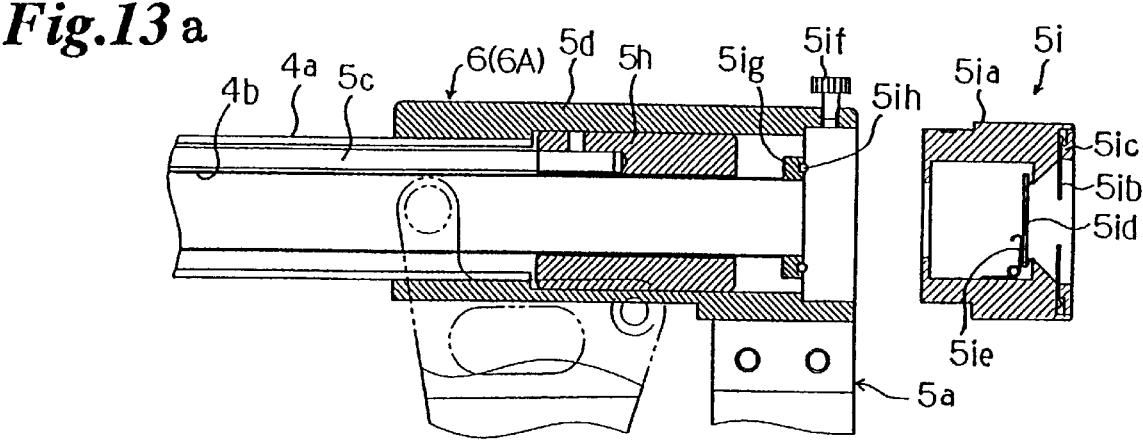
FIG. 13($a$) shows when the sealing mechanism is loaded according to a tissue excision and cutting apparatus of the present invention.
Figure 13:
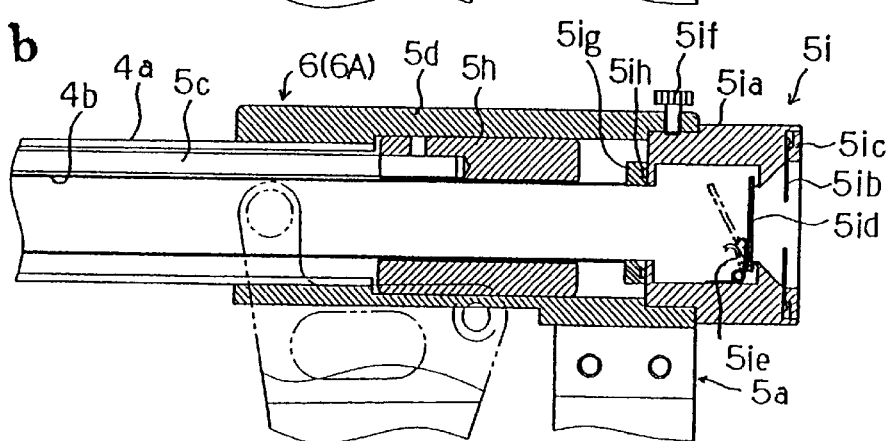
Figure 13:
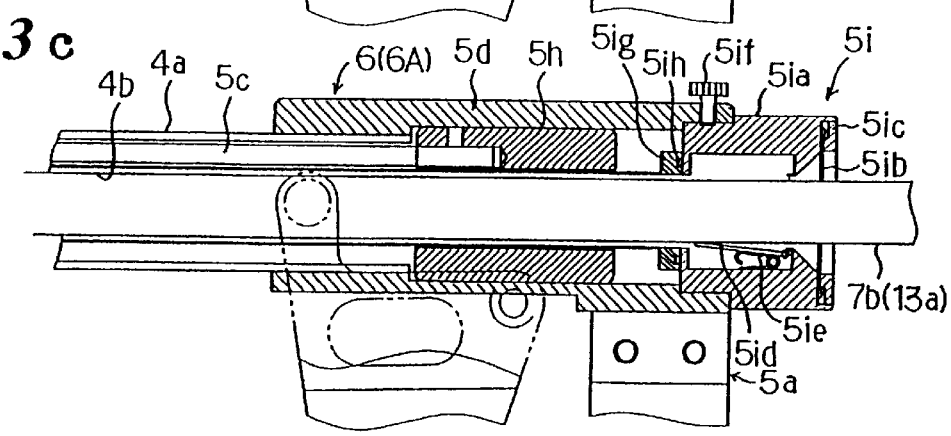

FIG. 13 is a partial vertical section explaining its sealing mechanism and FIG. 13(a) shows when the sealing mechanism is loaded, FIG. 13(b) shows after it is loaded, and FIG. 13(c) shows when the resection blade or the rotatable resection blade is inserted.

The sealing mechanism 5i is comprised of a sealing body 5ia, a sealing ring 5ib, a presser board 5ic, a sealing plate 5id, a spring 5ie, a setscrew 5if, an auxiliary ring 5ig, and an O-ring 5ih.

The sealing body 5ia is approximately cylindrical as shown in the figure and one end of the external diameter is detachably inserted into an insertion hole provided at the rear end of the open-close mechanism 5. A penetrating hole is provided in the inner diameter for securing the longitudinal penetrating passage 4 in sequence of the open-close mechanism 5.

The sealing ring 5ib is provided opposite to the inserted side of the open-close mechanism 5 with the sealing body 5ia and is fixed with the presser board 5ic. The sealing body 5ia is like a circular disc with a hole made of rubber and the diameter of the hole is a little smaller than that of the longitudinal penetrating passage 4. When the resection blade is inserted in the hole, the hole is designed to seal its external diameter.

The seal plate 5id is enforced by the spring 5ie so as to open and close the hole provided at the intermediate part of the seal body 5ia in axial direction. The setscrew 5if is provided at the rear end of the open-close mechanism 5 for fixing and holding the detachably inserted seal body 5ia.

The auxiliary ring 5ig is provided at the position which is the rear end of the forceps inner cylinder 4b comprising a double cylinder in the forceps cylinder 4a and also the seal body 5ia is contacted and it is formed with a groove for containing the O-ring 5ih. The O-ring 5ih is designed to keep sealing between the seal body 5ia and the forceps inner cylinder 4b when the seal body 5ia is inserted in the rear end of the open-close mechanism 5. The inner diameter part of the forceps inner cylinder 4b is formed the longitudinal penetrating passage 4.

The sealing mechanism 5i is constructed such that the seal body 5ia having the seal ring 5ib and the sealing plate 5id is detachably inserted into the rear end of the open-close mechanism 5 as shown in FIG. 13(a) and the mechanism 5i is fixed by the setscrew 5if as shown in FIG. 13(b), thereby exerting its function.

As shown in FIG. 13(b), when the resection blade or the rotatable resection blade isn't inserted in the longitudinal penetrating passage 4, the seal plate 5id of the sealing mechanism 5i is enforce by the spring 5ie so that the hole of the seal body 5ia is closed and the longitudinal penetrating passage 4 and outer air are sealed. Although the seal plate 5id is enforced by the spring 5ie, its enforcing power is set so as to fell down the seal plate 5id when pushed by the inserted resection blade.

As shown in FIG. 13(c), when the resection blade or the rotatable resection blade is inserted in the longitudinal penetrating passage 4, the seal plate 5id is pushed and fell down by the resection blade so as not to prevent the resection blade from inserting. The periphery of the blade 7b of the inserted resection blade or the guide cylinder 13a of the rotatable resection blade is sealed from outside by affected by the inner diameter of the sealing ring 5ib.

Accordingly, the longitudinal penetrating passage 4 is kept sealed whenever the resection blade is inserted or not so that outer air is prevented from entering in abdominal cavity and the endo-bag through the longitudinal penetrating passage 4 or especially pneumoperitoneum gas is prevented from leaking out while being filled in the endo-bag.

Because the seal body 5ia is exchangeable, it can be exchanged when polluted, thereby keeping safety without executing troublesome sterilization.

The above-mentioned forceps is explained as a member of the tissue excision and cutting apparatus, however it doesn't matter the kind of the resection blade or the rotatable resection blade which is used together with the forceps. The forceps, as mentioned above, has independent utility value and technical value. Therefore, it can be used as a resection forceps 6A (FIG. 12, FIG. 13) alone and has similar effect cooperating with the combined resection blade.

Next the drop-out prevention means and the suction means provided for the resection blade as an active means for preventing the sampled tissue sample will be explained.

FIG. 14 shows one embodiment of a holding craw provided at the internal tip of the resection blade or the rotatable resection blade. FIG. 14(a) is its front view and Fib. 14(b) is a partial vertical section.

A holding craw 7e provided at an inner circumference of the blade 7a of the resection blade 7 is the same one which is used for preventing dropping out offish after hooked by a fishhook and is one of drop-out prevention methods of the sampled tissue sample.

In this embodiment, the blade 7a is made of stainless steel capable of hardening, for example SUS440C, for keeping sharpness of the blade. It is different from the material used for the resection blade body 7b such as titanium or stainless steel of SUS304. Therefore, the blade 7a is integrated with the body 7b by a tight insertion of an insertion integration part 7g after appropriate procedures such as sharpening and hardening of the blade 7a are executed.

The holding craw 7e is formed such that a radius shape is formed by turnery and substantial part is ground from the entire circumference of the radius shape formed around the circumference so as to leave three holding craws 7e as shown in the figures.

If the holding craw is formed circumferential, it is excellent for drop-out prevention, however, contrarily the cut tissue sample which has been cut into cylindrical by the tip blade and fed in the inmost recesses of the resection blade 7 in turn is prevented from being fed into further inmost recess.

Therefore, the holding craw 7e is partially left and three holding craws are appropriate as shown in the figure, however from two to five holding craws may be provided.

According to such about three holding craws 7e doesn't hinder the tissue sample from being fed and can prevent the tissue sample from dropping out.

The holding craws are appropriately positioned not far from the tip of the blade 7a in the blade axis direction, more concretely, where the shortest one of the usually formed cylindrical tissue samples can be hooked. Further, the holding craws may be provided in a line as shown in the figure, however they may be provided in plural lines at different positions from the tip in the direction of the blade axis by differing circumferential position or at the same circumferential position.

Such a holding craw may be similarly provided for the rotatable resection blade 12 (FIG. 11) and such a case is shown as the parenthetic numerals in the figures such as a rotatable resection blade 12, a blade 12a, a body 12b, a holding craw 12e.

Figure 15:
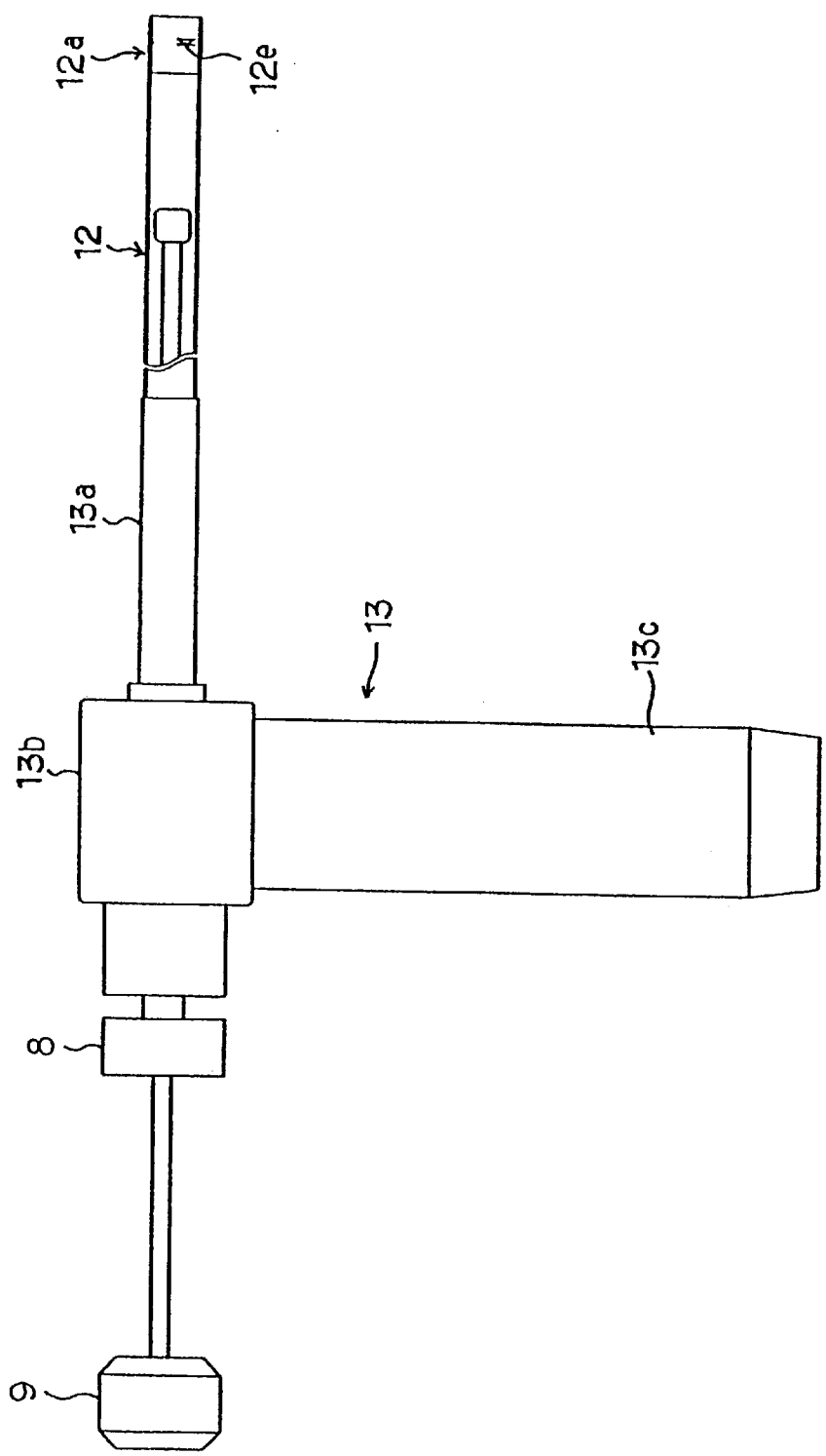
FIG. 15 is an external front view of one embodiment of a rotatable resection blade provided with holding craw as shown in FIG. 14.

FIG. 15 is an external front view of one embodiment of a rotatable resection blade provided with holding craw 12e as shown in FIG. 14.

The holding craw 12e can be similarly provided for a rotatable resection blade and have the same effect.

FIG. 16 shows another embodiment of a holding craw provided inside tip of a resection blade or a rotatable resection blade of the present invention. FIG. 16(a) is its front view and FIG. 16(b) is its partial vertical section.

The holding craw 7f is provided for the body 7b of the resection blade 7 comparing to the holding craw 7e of FIG. 14 and is formed by plastic forming of the blade body 7b made of lightweight titanium, and excellent for anti-corrosion, and plasticity or SUS304 stainless steel which is excellent for anti-corrosion and easy to be manufactured.

The holding craw 7f is designed t prevent the cut tissue sample from dropping out like the holding craw 7e of FIG. 14. However, the holding craw 7f is shaped by plastic forming with shearing and pressing against the relatively thin cylindrical part of the blade body 7b.

Its drop-out prevention effect isn't different from the holding craw 7e, however, it must be provided for the body 7b because of the manufacturing performance so that it must be provided at substantial distance from the tip of the blade 7a. In this point the holding craw 7f isn't suitable for preventing dropping out of a short tissue sample.

Both of the holding craw 7e and 7f may be provided.

The holding craw 7f can be provided for the rotatable resection blade 12 like the holding craw 7e and such a case is shown as parenthetic numbers in the figure.

Figure 17:
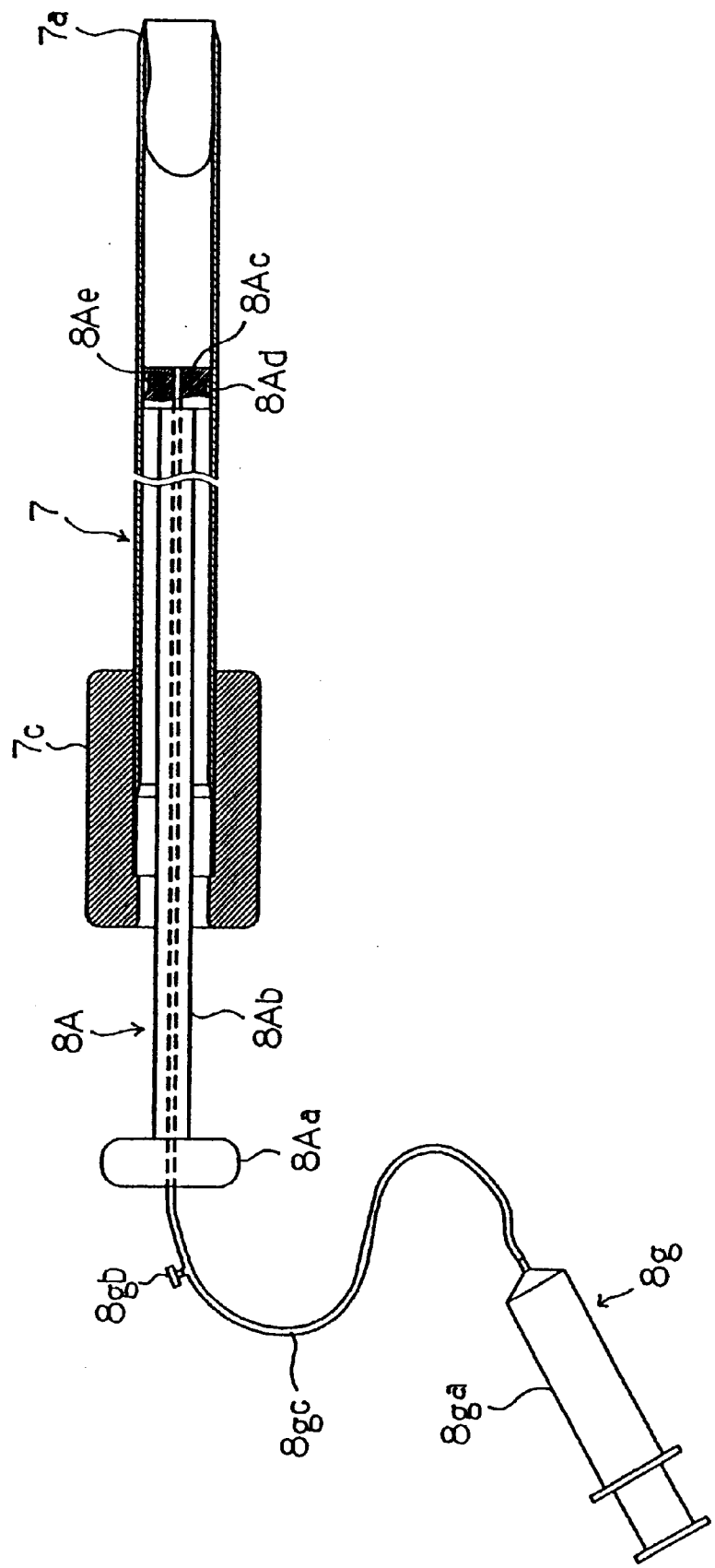
FIG. 17 is a partial vertical section explaining operation of one embodiment of a sealing rod used for a resection blade or a rotatable resection blade of the present invention.

FIG. 17 is a partial vertical section explaining operation of one embodiment of a sealing rod used for a resection blade or a rotatable resection blade of the present invention.

The sealing push rod 8A is constructed like the push rod 11 in FIG. 5 and they are different in that the sealing push rod 8A is provided with a sample suction means 8g actively generating suction force in place of the sealing rod 10, the sample suction means 8g is one embodiment of a suction means of the cut and sampled tissue sample.

The sealing push rod 8A itself is constructed with a rib 8Aa, an rod part 8Ab, a head 8Ac, an O-ring 8Ad, and an air vent hole 8Ae like the push rod 11 in FIG. 5 and they work like those for the push rod 11.

The sample suction means 8g detachably provided for the air vent hole 8Ae instead of the sealing rod 10 is comprised of a syringe 8ga, a switch valve 8gb, and a tube 8gc.

The sample suction means 8g isn't loaded before the sealing rod 8A is inserted in the resection blade 7 and it cuts and samples tissue so as not to disturb cutting and sampling of tissue by allowing communication of air from the air vent hole 8Ae.

However, as shown in FIG. 17, the simple suction means 8g is loaded after the tissue sample Ac is sampled, the switch valve 8gb is opened, and suction force is generated by operating the syringe 8ga so as to actively suck the sampled tissue sample Ac not to be dropped out.

After the resection blade 7 is moved at a predetermined position while keeping suction, the contained tissue sample Ac may be extruded by generating pressure force by operating the syringe 8ga of the sample such means 8g, or it may be extruded only by the operation of the sealing push rod 8A after removing the sample suction means 8g.

The switch valve 8gb may be closed after sucking with the syringe 8ga to keep suction force. When it can be replaced by the operation of the syringe 8ga, the switch valve 8gb isn't always required.

In this case a syringe is used as a sample of the sample suction means 8g because it is easily obtained at medical sites, however it isn't limited.

Figure 18A:
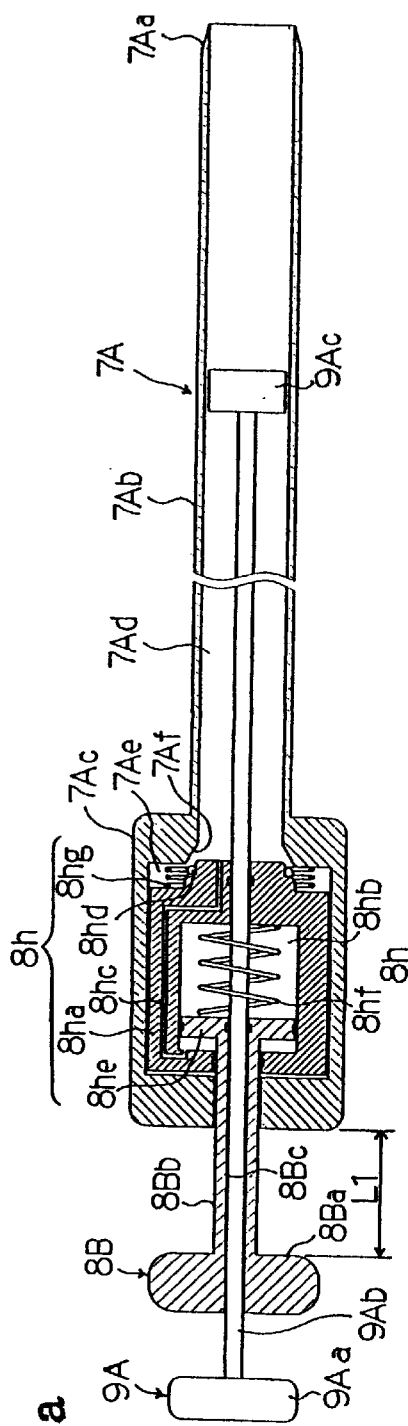
FIG. 18(a) is a partial vertical section before tissue is cut according to a tissue excision and cutting apparatus of the present invention.
Figure 18B:
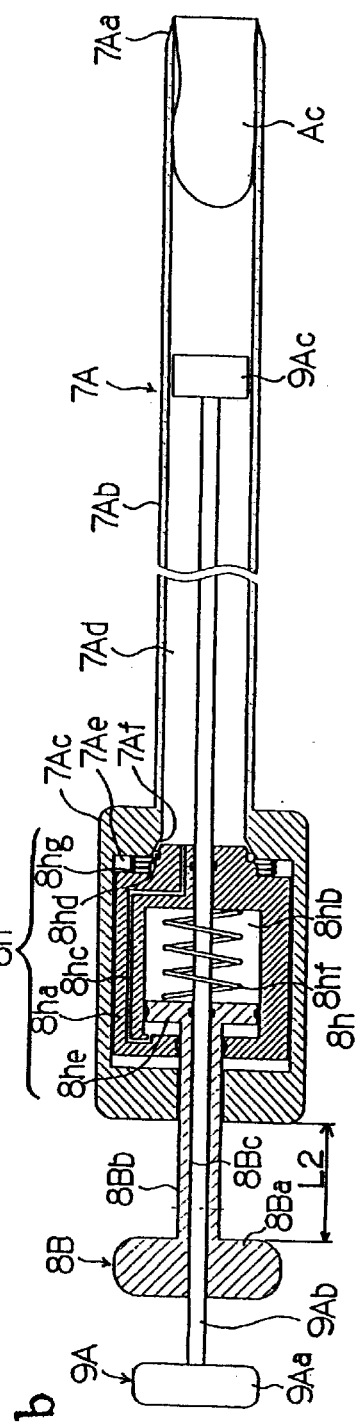
FIG. 18(b) is a partial vertical section after tissue is cut according to a tissue excision and cutting apparatus of the present invention.
Figure 18C:
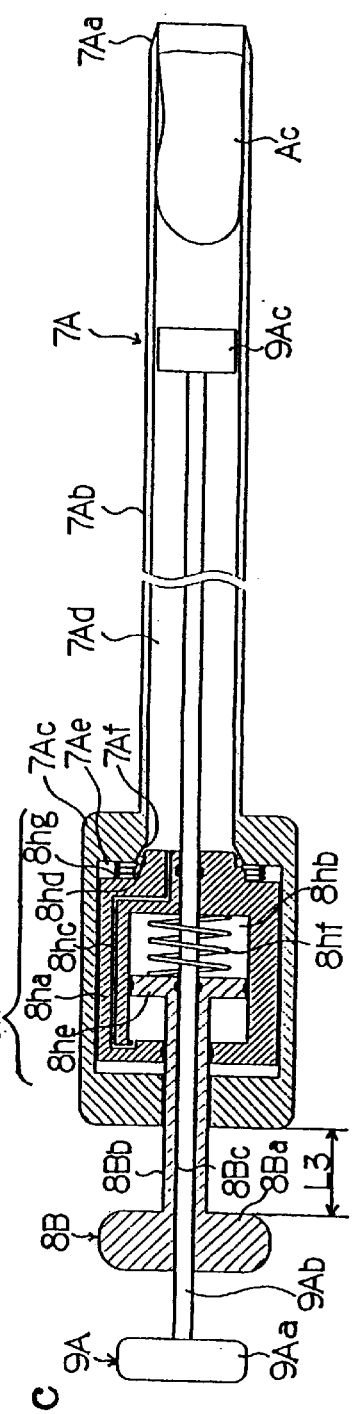
FIG. 18(c) is a partial vertical section when a tissue sample is suck and held according to a tissue excision and cutting apparatus of the present invention.

FIG. 18 explains operation of another embodiment of a sealing rod and a push rod used for a resection blade or a rotatable resection blade of the present invention. FIG. 18(a) is a partial vertical section before tissue is cut, FIG. 18(b) is a partial vertical section after tissue is cut, and FIG. 18(c) is a partial vertical section when a tissue sample is suck and held.

A sealing suction rod 8B and a push rod 9A are the same as the sealing rod 8 and the push rod 9 in FIG. 4. However, a sealing suction mechanism 8h is provided for the sealing suction rod 8B. The push rod 9A and a resection blade 7A are a little different from those in FIG. 4. The sealing suction rod 8B and the push rod 9A are another embodiment of the suction means of cut and sampled tissue sample.

The resection blade 7A is different from the resection blade 7 in FIG. 4 in that a container 7Ae containing the sealing suction mechanism 8h is included in a holding portion 7Ac corresponding to the sealing suction rod 8B provided with the sealing suction mechanism 8h. It also different in that a part connected from the container 7Ae to the hollow 7Ad in the resection blade 7A is a sealing tapered part 7Af. A blade 7Aa, a body 7Ab, the holding portion 7Ac and the hollow 7Ad are the same as those of the resection blade 7.

A rib 8Ba, an rod part 8Bb, and a push hole 8Bc of the sealing suction rod 8B are almost the same as those of the sealing rod 8. It is different in that a piston flange 8he to be contained in the sealing suction mechanism 8h is provided at the tip of the rod part 8Bb.

The sealing suction mechanism 8h is comprised of a sealing cylinder 8ha slidably contained in the container 7Ae of the resection blade 7A, an inner chamber 8hb provided therein, a communication passage 8hc for communicating air between the inner chamber 8hb and the hollow 7Ad of the resection blade 7A, an O-ring 8hd which is provided at the tip of the hollow 7Ad side of the sealing cylinder 8ha and exerts sealing function when it contacts with the sealing tapered part 7Af of the resection blade 7A, the above-mentioned piston flange 8he sliding airtightly in the inner chamber 8hb, a spring 8hf enforcing the piston flange 8he in the left direction in FIG. 18, and a spring 8hg provided at the tip of the hollow 7Ad of the sealing cylinder 8ha and enforcing the sealing cylinder 8ha in the left direction of FIG. 18 by generating enforce power between an inner wall of the container 7Ad of the resection blade 7A.

The spring 8hf is designed to require larger force than the spring 8hg to be compressed the same length so that the spring constant (load/distortion) of the spring 8hf becomes larger than the spring 8hg.

The push rod 9A is comprised of a rib 9Aa, an rod part 9Ab, and a head 9Ac like those of the push rod 9 in FIG. 4. The push hole 8Bc of the sealing suction rod 8B, the spring 8hf and the sealing cylinder 8ha of the sealing suction mechanism 8h are penetrated by the rod part 9Ab and the push hole 8Bc and the sealing cylinder 8ha are sealed by an appropriate sealing means such as an O-ring so as to be slidable keeping airtight.

The holding portion 7Ac of the resection blade 7A is constructed such that the container 7Ae can be opened, the sealing cylinder 8ha of the sealing suction mechanism 8h is constructed so as to be able to open the inner chamber 8hb, and the head 9Ac of the push rod 9A is constructed detachable. As shown in the figure they can be disassembled after assembled and used.

When tissue sample is cut and sampled by means of the sealing suction rod 8B and the push shaft 9A, the sealing suction rod 8B is positioned freely as shown in FIG. 18(a). The distance between the rib 8Ba of the sealing suction rod 8B and the holding portion 7Ac of the resection blade 7A is defined as L1. The push rod 9A is positioned so as to keep enough space for containing the cut tissue sample in the hollow 7Ad forward of the head 9Ac. The hollow 7Ad in the resection blade 7A is communicated with air because of the space between the sealing suction rod 8B, and sealing cylinder 8ha and the container 7Ae of the holding portion 7Ac.

After tissue sample is cut by the tissue excision and cutting apparatus 1 having the resection blade 7A, only the sealing suction rod 8B is pushed as shown in FIG. 8(b). Because the spring 8hg is stronger than the spring 8hf, the sealing cylinder 8ha slides forward in the container 7Ae of the holding portion 7Ac by the just distance that the sealing suction rod 8B is pushed. The O-ring 8hd provided at the tip of the sealing cylinder 8ha contacts with the sealing tapered part 7Af of the holding portion 7Ac and the hollow 7Ad in the resection blade 7A is kept airtight by the sealing cylinder 8ha. The distance between the rib 8Ba of the sealing suction rod 8B and the holding portion 7Ac of the resection blade 7A is defined as L2.

When only the sealing suction rod 8B is further pushed, the sealing cylinder 8ha doesn't further slide and only the sealing suction rod 8B slides forward against the sealing cylinder 8ha while compressing the spring 8hf as shown in FIG. 18(c). The piston flange 8he of the sealing suction rod 8B slides forward while keeping airtight in the inner chamber 8hb of the sealing cylinder 8ha so that suction force is generated in the space in the rear of the piston flange 8he and is transmitted to the hollow 7Ad of the resection blade 7A via the communication passage 8hc. Accordingly suction force is generated in the hollow 7Ad. The distance between the rib 8Ba of the sealing suction rod 8B and the holding portion 7Ac of the resection blade 7A is defined as L3.

Sealing and suction can be achieved and the cut and sampled tissue sample Ac can be easily suck and grasped simply by pushing the sealing suction rod 8B from a free condition L1 to the distances L2 and L3. After the resection blade 7A holding the tissue sample Ac is moved at a predetermined place, the sealing suction rod 8B can be returned to its original free position L1 by the force of repulsion of the springs 8hf, 8hg only by releasing pushing of the sealing suction rod 8B. Then the tissue sample Ac can be easily extruded by operating the push rod 9A.

It is more convenient that a lock means which can keep the sealing suction rod 8B at the distance L3 and can be easily released is provided if required.

FIG. 19(a)–FIG. 19(f) explain operation of a suction and sampling means used for a resection blade or a rotatable resection blade of the present invention.

This suction and sampling means 14 is provided for actively collecting the tissue sample cut and sampled by the resection blade in a sample container not only by sucking and grasping but also by utilizing air suction force. It is another embodiment of a suction means of tissue sample.

The suction and sampling means 14 is comprised of a sample container 14a which is a bag made of mesh material for passing suction force and provided with an attachment opening, a connecting means 14b for connecting the sample container 14a and a connecting part 7Ba at the rear of a resection blade 7B, and a cover 14c provided for the connecting means 14b and covering the sample container 14a fully for keeping airtight.

The resection blade 7B connected with the suction and sampling means 14 is different from the above-mentioned resection blade 7, 7B in that it is provided with the connecting part 7Ba at its rear end. A connecting groove 7Bb is provided for the connecting part 7Ba for fixing the connecting means 14b of the suction and sampling means 14 and a connecting pin 14ba is vertically provided for the connecting means 14b to be inserted in the groove 7Bb.

When the suction and sampling means 14 is used, at first the connecting means 14b is set for the sample holder 14a (FIGS. 19(a), (b)), then the cover 14c is covered (FIG. 19(c)), and the assembled suction and sampling means 14 is connected and fixed to the connecting part 7Ba of the resection blade 7B by utilizing association of the connecting pin 14ba and the connecting groove 7Bb (FIG. 19(d)).

Then suction force is supplied to the suction and sampling means 14 from an suction air source (not shown) and the tissue sample cut and sampled by the resection blade 7B is suck and collected (FIG. 19(e)). This suction and collection may be repeated until a purpose is accomplished more than one time.

After suck and collection are finished, the suction and sampling means 14 is removed from the resection blade 7B and disassembled. The tissue sample collected in the sample container 14a is taken out at a predetermined place (FIG. 19(f)).

Accordingly tissue samples taken out several times can be easily collected and taken out in bulk.

This suction and sampling means can be used for a rotatable resection blade. Both of the above-mentioned holding craw and several suction means for preventing dropping out of tissue sample can be applied for a resection blade or a rotatable resection blade. In such a case both effects can be synergistically brought out.

While the present invention has been particularly shown and described with reference to preferred embodiments thereof, it will be understood by those skilled in the art that the foregoing and other changes in form and details can be made therein without departing from the spirit and scope of the invention.

What is claimed is:

1. A tissue excision and cutting apparatus used by being inserted into a trocar, for cutting off a part of tissue for sampling in a laparoscopic surgery comprising:

a forceps comprising a clamp provided at the end of said forceps for grasping a part of tissue to be cut off, said clamp having a movable jaw pivotally joined to a fixed jaw with a chopping block at its end, an open-close mechanism with an operation part for opening and closing said movable jaw against said fixed jaw, and a longitudinal penetrating passage between said fixed jaw and said movable jaw, a resection blade having an inner hollow cylinder body formed with a circumferential cutting edge at its end, said resection blade being inserted movably back and forth into said penetrating passage and said cutting edge running into said chopping block when cutting off said part of tissue by moving the resection blade forth, and a rotary driving mechanism provided in said apparatus for rotating said resection blade.

2. The tissue excision and cutting apparatus as set forth in claim 1, wherein said operation part of said open-close mechanism is constructed such that it can be held by one hand and said movable jaw can be opened and closed by manual operation of said one hand.

3. The tissue excision and cutting apparatus as set forth in claim 1, wherein said chopping block piece is formed with a blade receiving surface so as to contact with the whole circumference of said blade of resection blade.

4. The tissue excision and cutting apparatus as set forth in claim 1, wherein said passage is at the rear end provided with an insertion opening for said resection blade and wherein said insertion opening is further provided with a sealing valve mechanism for isolating ventilation into the open air even when said resection blade is put in and out.

5. The tissue excision and cutting apparatus as set forth in claim 4, wherein said sealing valve mechanism is detachable and exchangeable for said insertion opening.

6. The tissue excision and cutting apparatus as set forth in claim 1, wherein said resection blade further coprises a sealing rod for airtightly sealing the inner of said hollow cylinder body of said resection blade and a push shaft for outwardly extruding a part of tissue which is cut off by said blade and held in said hollow cylinder body as a sample piece, by being airtightly inserted into said cylinder body from a push hole provided at the rear end of said sealing rod.

7. The tissue excision and cutting apparatus as set forth in claim 1, wherein said resection blade further comprises a sealing push rod which is airtight inserted into said hollow cylinder body from an insertion opening provided at the rear end of said cylinder body, and a sample suction means connected to said sealing push rod for keeping said inner portion of said hollow cylinder body airtight condition to hold the cut off tissues as a sample piece by said resection blade in said cylinder body.

8. The tissue excision and cutting apparatus as set forth in claim 1, wherein said resection blade further comprises a sealing suction rod into which a sealing suction mechanism is incorporated, said sealing suction rod airtightly sealing the inner portion of said resection blade and keeping airtight condition in the inner portion of said cylinder body to hold the cut off tissue as a sample piece by said resection blade, and a push rod for outward extruding a part of tissue cut off by said resection blade and held in said hollow cylinder body as a sample piece, by being airtightly inserted into said hollow cylinder body from a push hole provided at the rear end of said sealing suction rod.

9. The tissue excision and cutting apparatus as set forth in claim 1, wherein said resection blade further comprises a suction sampling collecting means detachably connected to the rear end of said hollow cylinder for sucking to collect the cut off tissue as a sample piece by said resection blade.

10. The tissue excision and cutting apparatus as set forth in claim 1, wherein said resection blade is in an inner surface adjacent to its tip end provided with a holding craw for preventing dropping out of the cut off tissue as a sample piece by said resection blade.

11. The tissue excision and cutting apparatus used by being inserted into a trocar, for cutting off a part of tissue for sampling in a laparoscopic surgery comprising:

a forceps comprising a clamp provided at the end of said forceps for grasping a part of tissue to be cut off, said clamp having a movable jaw pivotally joined to a fixed jaw with a chopping block at its end, an open-close mechanism with an operation part for opening and closing said movable jaw against said fixed jaw, and a longitudinal penetrating passage, within said fixed jaw and said movable jaw, and a resection blade capable of being rotated by a rotary driving mechanism provided in said apparatus and having an inner hollow cylinder body formed with a circumferential cutting edge at its end, said resection blade being inserted movably back and forth into said penetrating passage and said cutting edge running into said chopping block when cutting off said part of tissue by moving the resection blade forth;

whereby said resection blade is capable of containing therein the tissue having been cut off with said resection blade against said chopping block.

* * * * *